US011807855B2

(12) United States Patent
Assaraf et al.

(10) Patent No.: US 11,807,855 B2
(45) Date of Patent: Nov. 7, 2023

(54) SELECTION VECTORS AND METHODS OF SELECTING EUKARYOTIC HOST CELLS

(71) Applicant: Novartis AG, Basel (CH)

(72) Inventors: Yehuda G Assaraf, Misgav (IL); Thomas Jostock, Neuenburg am Rhein (DE); Hans-Peter Knopf, Schallstadt (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/907,866

(22) PCT Filed: Jul. 29, 2014

(86) PCT No.: PCT/IB2014/063517
§ 371 (c)(1),
(2) Date: Jan. 27, 2016

(87) PCT Pub. No.: WO2015/015419
PCT Pub. Date: Feb. 5, 2015

(65) Prior Publication Data
US 2016/0177318 A1 Jun. 23, 2016

Related U.S. Application Data

(60) Provisional application No. 61/860,439, filed on Jul. 31, 2013.

(51) Int. Cl.
*C12N 15/65* (2006.01)
*C12N 15/85* (2006.01)
*C07K 14/705* (2006.01)
*C07K 16/00* (2006.01)
*C12N 15/69* (2006.01)

(52) U.S. Cl.
CPC ............ *C12N 15/65* (2013.01); *C07K 14/705* (2013.01); *C07K 16/00* (2013.01); *C12N 15/85* (2013.01); *C12N 15/69* (2013.01); *C12N 2800/40* (2013.01)

(58) Field of Classification Search
CPC ........ C12N 15/65; C12N 15/85; C12N 15/69; C12N 2800/40; C07K 14/705; C07K 16/00; C12P 21/02
See application file for complete search history.

(56) References Cited

U.S. PATENT DOCUMENTS

| | | | |
|---|---|---|---|
| 4,771,036 A | 9/1988 | Pigiet et al. | |
| 5,830,698 A | 11/1998 | Reff et al. | |
| 5,879,686 A | 3/1999 | Blake et al. | |
| 6,106,825 A | 8/2000 | Moyer et al. | |
| 6,716,835 B1 | 4/2004 | Picaud et al. | |
| 8,071,745 B2 | 12/2011 | Leveillard et al. | |
| 8,518,695 B2 | 8/2013 | Leveillard et al. | |
| 8,779,093 B2 | 7/2014 | Leveillard et al. | |
| 8,962,274 B2 | 2/2015 | Jostock et al. | |
| 9,315,844 B2 | 4/2016 | Jostock et al. | |
| 9,534,226 B2 | 1/2017 | Jostock et al. | |
| 9,994,866 B2 | 6/2018 | Jostock et al. | |
| 10,767,186 B2 | 9/2020 | Assaraf et al. | |
| 11,174,494 B2 | 11/2021 | Jostock et al. | |
| 2004/0148647 A1 | 7/2004 | Enenkel et al. | |
| 2006/0275794 A1 | 12/2006 | Carrino et al. | |
| 2010/0330572 A1* | 12/2010 | Assaraf ................. | C12N 15/85 435/6.13 |
| 2011/0306092 A1 | 12/2011 | Jostock et al. | |
| 2011/0306095 A1 | 12/2011 | Jostock et al. | |
| 2012/0108523 A1 | 5/2012 | Leveillard et al. | |
| 2012/0108657 A1 | 5/2012 | Leveillard et al. | |
| 2012/0276579 A1 | 11/2012 | Assaraf et al. | |
| 2013/0287738 A1 | 10/2013 | Leveillard et al. | |
| 2014/0154739 A1 | 6/2014 | Jostock et al. | |
| 2014/0295489 A1 | 10/2014 | Assaraf et al. | |
| 2016/0177318 A1 | 6/2016 | Assaraf et al. | |
| 2016/0355828 A1 | 12/2016 | Assaraf et al. | |
| 2017/0067077 A1 | 3/2017 | Jostock et al. | |
| 2018/0265891 A1 | 9/2018 | Jostock et al. | |
| 2020/0370055 A1 | 11/2020 | Assaraf et al. | |

FOREIGN PATENT DOCUMENTS

| | | | |
|---|---|---|---|
| CA | 2507714 A1 | 6/2004 | |
| EP | 0724639 A1 | 8/1996 | |
| JP | 2012-235787 | 12/2012 | |
| KR | 10-2011-0119837 A | 11/2011 | |
| WO | 2004081167 A2 | 9/2004 | |
| WO | 2005073375 A1 | 8/2005 | |
| WO | 2007096399 A2 | 8/2007 | |
| WO | 2007131774 A1 | 11/2007 | |
| WO | 2009/080759 A1 | 7/2009 | |
| WO | 2010022961 A1 | 3/2010 | |
| WO | 2010/097239 A1 | 9/2010 | |
| WO | 2010/097240 A1 | 9/2010 | |
| WO | 2015/015419 A1 | 2/2015 | |

OTHER PUBLICATIONS

Grapp et al., Brain, 2012, vol. 135, pp. 2022-2031.*
Mangiarottei et al., Journal of Cellular Biochemistry, 2001, vol. 81 pp. 488-498.*
Chen et al., Nature, vol. 500, Aug. 22, 2013, pp. 486-490.*
Van Blokland et al. (2011) Methods to create a stringent selection system for mammalian cell lines. Cytotechnology, 63:371-384 (Year: 2011).*
Shen et al. (1997) Identification of Amino Acid Residues that Determine the Differential Ligand Specificities of Folate Receptors alpha and beta. Biochemistry, 36:6157-6163 (Year: 1997).*

(Continued)

*Primary Examiner* — Neil P Hammell
*Assistant Examiner* — Morgan T Lindgren Baltzell
(74) *Attorney, Agent, or Firm* — Nelson Mullins Riley & Scarborough LLP; Jane E. Remillard, Esq.; Jill Gorny Sloper, Esq.

(57) ABSTRACT

The disclosure is directed to an expression vector or a combination of at least two expression vectors for producing a polypeptide of interest, the vector or vectors comprising a polynucleotide encoding a mutated folate receptor as a selectable marker. The disclosure also relates to host cells, selection methods and methods for producing polypeptides with high yield.

6 Claims, 3 Drawing Sheets

Specification includes a Sequence Listing.

(56) References Cited

OTHER PUBLICATIONS

Ramamoorthy, et al. (2007) In silico analysis of functionally important residues in folate receptors. Bioinformation, 2(4):157-162 (Year: 2007).*
U.S. Appl. No. 15/988,141, Jan. 1, 2021.
Lesovaya E.A. et al. "The Therapy of Cancer Diseases by Means of Targeted Complement Activation" Jul. 2008 (Abstract only).
Eaton D. et al., "Construction and characterization of an active factor viii variant lacking the central one-third of the molecule", Biochemistry, vol. 25(26) :8343-8347 (1986).
Folate receptor alpha precursor [*Homo sapiens*], NCBI Reference Sequence: NP 00793.1, 1 www.ncbi.nlm.nih.gov/protein/4758400sat=12&satkey=2867627, p. 1-3, Feb. 11, 2008.
Grillari J., et al., : "Analysis of alternations in gene expression after amplification of recombinant genes in CHO cells", Journal of Biotechnol., vol. 87L 59-65 (2001).
Levitt N. et al., "Definition of an efficient synthetic poly(A) site," Genes & Development, vol. 3(7):1019-1025 (1989).
Neuberger M: "Expression and regulation of immunoglobulin heavy chain gene transfected into lymphoid cells," The EMBO Journal, vol. 2(8):1373-1378 (1983).
Oumard A. et al., "Recommended method for chromosome exploitation: RMCE-based cassette-exchange systems in animal cell biotechnology", Cytotechnology, vol. 50:93-108 (2006).
Rothem L et al: "The reduced folate carrier gene is a novel selectable marker for recombinant protein overexpression", Molecular Pharmacology, American Society for Pharmacology and Experimental Therapeutics, Baltimore, MD vol. 68, No. 3, pp. 616-624, 2005.
Salazar M D et al., "The folate receptor: what does it promise in tissue-targeted therapeutics'?", Cancer Metastasis Rev., vol. 26(1):141-152 (2007).
Sorrell D. et al., "Targeted modification of mammalian genomes," Biotechnology Advances, vol. 23: 431-469 (2005).
Spandidos, et al., "Linkage of markers controlling consecutive biochemical steps in CHO cells as demonstrated by chromosome transfer," Cell, vol. 12: 235-242 (1977).
Spinella, et al., "Comparison of methotrexate polyglutamylation L1210 leukemia cells with influx is mediated by the reduced folate carrier or the folate receptor; tack of evidence for influx route-specific effects" Biochemical Pharmacology, vol. 52: 703-712 (1996).
Subramani S. et al., "Expression of the mouse dihydrofolate reductase complementary deoxyribonucleic acid in simian virus 40 vectors", Molecular and Cellular Biology, vol. 1(9):854-864(1981).
Wurm F.: "Production of recombinant protein therapeutics in cultivated mammalian cells," Nature Biotechnology, vol. 22:1393-1398 (2004).
Zhu W. et al., "The rate of folate receptor alpha (FRalpha) synthesis in folate depleted CHL cells is regulated by a translational mechanism sensitive to media folate levels while stable overexpression of its mRNA is mediate by gene amplification and an increase in transcript half-life," Journal of Cellular Biochemistry, vol. 81(2):205-219 (2001).
Birch, J. et al., "Antibody production," Advanced Drug Delivery Reviews, vol. 58: 671-685 (2006).
Jostock, T., "Expression of an Antibody in Mammalian Cells," Chapter 1, M. Al-Rubeai (ed.), Antibody Expression and Production, Cell Engineering 7, 24 pages (2011).
Lalonde, M-E. et al., "Therapeutic glycoprotein production in mammalian cells," Journal of Biotechnology, vol. 251:128-140 (2017).
Berry, M. J. et al., Substitution of cysteine for selenocysteine in type I iodothyronine deiodinase reduces the catalytic efficiency of the protein but enhances its translation, Endocrinology, vol. 131, No. 4, pp. 1848-1852, 1992.
Gasser, B. et al., Antibody production with yeasts and filamentous fungi: on the road to large scale?, Biotechnology Letters, vol. 29, No. 2, pp. 201-212, 2007.
Pakula, A.A., et al, Genetic analysis of protein stability and function, Annual Review of Genetics, vol. 23, No. 1, pp. 289-310, 1989.
U.S. Appl. No. 13/203,546, filed Aug. 26, 2011, Thomas Jostock.
U.S. Appl. No. 14/174,228, filed Feb. 6, 2014, Thomas Jostock.
U.S. Appl. No. 13/203,610, filed Aug. 26, 2011, Thomas Jostock.
U.S. Appl. No. 15/356,748, filed Nov. 21, 2016, Thomas Jostock.
U.S. Appl. No. 15/988,141, filed May 24, 2018, Thomas Jostock.
U.S. Appl. No. 12/808,704, filed Jun. 17, 2010, Yehuda G. Assaraf.
U.S. Appl. No. 13/495,043, filed Jun. 13, 2012, Yehuda G. Assaraf.
U.S. Appl. No. 14/275,304, filed May 12, 2014, Yehuda G. Assaraf.
U.S. Appl. No. 15/233,726, filed Aug. 10, 2016, Yehuda G. Assaraf.
U.S. Appl. No. 16/986,505, filed Aug. 6, 2020, Yehuda G. Assaraf.
U.S. Appl. No. 13/203,546, Oct. 31, 2014.
U.S. Appl. No. 13/203,546, Jun. 12, 2014.
U.S. Appl. No. 13/203,546, Nov. 6, 2013.
U.S. Appl. No. 13/203,546, May 16, 2013.
U.S. Appl. No. 13/203,546, Feb. 25, 2013.
U.S. Appl. No. 14/174,228, Dec. 11, 2015.
U.S. Appl. No. 14/174,228, Sep. 4, 2015.
U.S. Appl. No. 14/174,228, Apr. 17, 2016.
U.S. Appl. No. 13/203,610, Aug. 23, 2016.
U.S. Appl. No. 13/203,610, Dec. 3, 2015.
U.S. Appl. No. 13/203,610, Jan. 2, 2015.
U.S. Appl. No. 13/203,610, Jul. 2, 2014.
U.S. Appl. No. 13/203,610, Feb. 11, 2014.
U.S. Appl. No. 15/356,748, Jan. 25, 2018.
U.S. Appl. No. 15/356,748, Jun. 30, 2017.
U.S. Appl. No. 15/356,748, Jan. 27, 2017.
U.S. Appl. No. 15/988,141, Mar. 19, 2020.
U.S. Appl. No. 15/988,141, Nov. 7, 2019.
U.S. Appl. No. 12/808,704, Dec. 15, 2011.
U.S. Appl. No. 12/808,704, Jun. 22, 2011.
U.S. Appl. No. 13/495,043, Dec. 11, 2013.
U.S. Appl. No. 13/495,043, Apr. 15, 2013.
U.S. Appl. No. 13/495,043, Sep. 18, 2012.
U.S. Appl. No. 14/275,304, Jan. 12, 2016.
U.S. Appl. No. 14/275,304, Aug. 12, 2015.
U.S. Appl. No. 14/275,304, May 22, 2015.
U.S. Appl. No. 15/233,726, May 6, 2020.
U.S. Appl. No. 15/233,726, Sep. 12, 2019.
U.S. Appl. No. 15/233,726, Jul. 20, 2018.
U.S. Appl. No. 15/233,726, Oct. 31, 2017.
U.S. Appl. No. 15/233,726, Jun. 6, 2017.
Shen Feng et al : "Identification of amino acid residues that determine the differential ligand specificities of folate receptors alpha and beta", Biochemistry, vol. 36. No. 20; 1997; pp. 6157-6163.
K. M. Maziarz et al : "Complete Mapping of Divergent Amino Acids Responsible for Differential Ligand Binding of Folate Receptors and", Journal of Biological Chemistry, vol. 274. No. 16; Apr. 16, 1999; p. 11086-11091.
P. Rich et al; "Secukinumab induction and maintenance therapy in moderate to severe plaque psoriasis: a randomized, double-blind, placebo-controlled, phase II regimen-finding study"; British Journal of Dermatology; Sep. 23, 2012; pp. 402-411.

* cited by examiner

SELECTION VECTORS AND METHODS OF SELECTING EUKARYOTIC HOST CELLS

FIELD OF THE DISCLOSURE

The present disclosure relates to a novel selection system that is based on the use of a mutated folate receptor as selectable marker for the selection of host cells, in particular mammalian host cells, expressing a polypeptide of interest. The invention provides suitable expression vectors, host cells and methods for selecting host cells expressing a recombinant polypeptide of interest with a high yield. Furthermore, the present invention pertains to a method for efficiently producing recombinant polypeptides with a high yield.

BACKGROUND OF THE DISCLOSURE

The ability to clone and express products of interest such as recombinant peptides and proteins in large amounts has become increasingly important. The ability to purify high levels of proteins is important in the human pharmaceutical and biotechnological field, for example for producing protein pharmaceuticals as well as in the basic research setting, for example for crystallizing proteins to allow the determination of their three dimensional structure. Proteins that are otherwise difficult to obtain in quantity can be overexpressed in a host cell and subsequently isolated and purified.

The choice of an expression system for the production of recombinant proteins depends on many factors, including cell growth characteristics, expression levels, intracellular and extracellular expression, post-translational modifications and biological activity of the protein of interest, as well as regulatory issues and economic considerations in the production of therapeutic proteins. Key advantages of mammalian cells over other expression systems such as bacteria or yeast are the ability to carry out proper protein folding, complex N-linked glycosylation and authentic O-linked glycosylation, as well as a broad spectrum of other post-translational modifications. Due to the described advantages, eukaryotic and in particular mammalian cells are currently the expression system of choice for producing complex therapeutic proteins such as monoclonal antibodies.

The most common approach to obtain high expressing host cells (also called high producers) generates an appropriate expression vector for expressing the polypeptide of interest as a first step. The expression vector drives the expression of the polynucleotide encoding the polypeptide of interest in the host cell and provides at least one selectable marker for generating the recombinant cell line.

One established procedure for obtaining high producing cell lines expressing the polypeptide of interest with high yield is the stable transfection of the host cells. The polypeptide of interest is then secreted into the culture medium and can be obtained in large quantities therefrom. However, the stable integration into the genome is a rare event and only a small subset of stably transfected cells are high producers.

Selectable markers and selection systems are widely used in order to obtain host cells expressing a polypeptide of interest with high yield. Respective systems are also useful to generate and identify stably transfected clones. The primary goal of using respective selectable markers and selection systems is to introduce a selectable gene which upon exposure to selective growth conditions allows the identification of cells capable of high-level production of the recombinant products of interest. Established selectable markers include for example dihydrofolate reductase (DHFR) or glutamine synthetase (GS).

Another selection system is based on the reduced folate carrier selection system. The reduced folate carrier (RFC) is a ubiquitously expressed membrane glycoprotein that serves as the major transporter for the uptake of reduced folates such as 5-methyl-THF and 5-formyl-THF. However, RFC displays a very poor affinity for the oxidized folate, folic acid. Hence, cells that lack the expression of RFC or have been deleted for the genomic RFC locus can serve as recipients for the transfection of the selectable marker gene RFC under conditions in which reduced folates such as 5-formyl-THF are gradually deprived from the growth medium thereby forcing the cells to express increased levels of the this folate transporter. There are several disadvantages for the RFC selection system: a) One must use RFC-null recipient cells in which the endogenous RFC locus has been knocked out or inactivated by targeted knockout or loss of function mutations. b) RFC has an extremely poor transport affinity for folic acid and thus this oxidized folate cannot be used for selection. c) As opposed to the folate-receptor based system (see below) that is a unidirectional folate uptake system, RFC is a bi-directional folate transporter that exhibits equally potent import and export of folates. This implies that under conditions of folate deprivation, RFC overexpression may be detrimental to the recipient cells that further export folate via the overexpressed RFC.

A further selection system that was proposed recently is based on the use of a folate receptor such as the folate receptor alpha as selectable marker. This system is described in WO2009/080759. This system has several advantages in that for selection, no toxic substances are needed and furthermore, the endogenous folate receptor of the host cell does not need to be knocked out. A further selection system that is based on the use of the folate receptor as selectable marker is described in WO 2010/097240.

Folate receptors and mutants thereof are described e.g. in Shen et al "Identification of amino acid residues that determine the differential ligand specificities of folate receptors alpha and beta" (Biochemistry 1997, 36, 6157-6163). Mutations in folate receptor alpha associated with medical disorders are also described. Amino acid positions in folate receptors were also analysed in Ramamoorthy et al "In silico analysis of functionally important residues in folate receptors" (Bioinformation 2 (4): 157-162 (2007)).

A high stringency selection system is crucial to select and thus enrich high producing cells from the transfected population. The higher the stringency of the selection system, the lower the number of low producers after the selection process and the higher the chance to find the very rare overproducing clones. Furthermore, there is a great need to provide a selection system that allows to obtain the high producing clones more rapidly than the prior art methods.

It is the object of the present invention to provide a stringent selection system for selecting host cells producing a polypeptide of interest with high yield, as well as suitable expression vectors and host cells. In particular, it is the aim of the present invention to provide a novel selection system that has certain advantages over prior art selection systems mentioned above.

SUMMARY OF THE DISCLOSURE

The present disclosure pertains to a selection system that is suitable for selecting host cells expressing a polypeptide of interest with a high yield. Said selection system is based on the use of a mutated functional membrane bound folate receptor as a selectable marker. Inter alia, said selection system allows a more stringent and faster selection of high producers than a selection system which uses a corresponding wild type functional membrane bound folate receptor as a selectable marker.

According to a first aspect, the present disclosure provides an expression vector or a combination of at least two expression vectors comprising:
- a) a polynucleotide encoding a mutated folate receptor as selectable marker, wherein the mutated folate receptor has a decreased folate binding affinity compared to the wild type folate receptor and
- b) at least one polynucleotide encoding a polypeptide of interest, wherein when said expression vector or combination of at least two expression vectors is introduced into a host cell, the polypeptide of interest is secreted from said host cell.

According to a second aspect, the present invention pertains to a host cell the viability of which is dependent on folate uptake comprising
- a) an introduced polynucleotide encoding a mutated folate receptor which has a decreased folate binding affinity compared to the wild type folate receptor as selectable marker
and
- b) at least one introduced polynucleotide encoding a polypeptide of interest wherein said polypeptide of interest is secreted from said host cell.

According to a third aspect, the present disclosure pertains to a method for producing a host cell according to the second aspect of the present invention, comprising the step of introducing into a host cell the viability of which is dependent on folate uptake at least
- a) a polynucleotide encoding a mutated folate receptor which has a decreased folate binding affinity compared to the wild type folate receptor as selectable marker
and
- b) at least one polynucleotide encoding a polypeptide of interest, wherein the polypeptide of interest is secreted from said host cell.

According to a fourth aspect, the present disclosure provides a method for selecting at least one host cell capable of expressing a polypeptide of interest, comprising
- a) providing a plurality of host cells according to the second aspect;
- b) culturing said plurality of host cells in a selective culture medium comprising folate in a limiting concentration;
and
- c) obtaining at least one host cell expressing the polypeptide of interest.

According to a fifth aspect, the present disclosure pertains to a process for producing a polypeptide of interest, comprising
- a) culturing a host cell according to the second aspect and/or a host cell selected according to the fourth aspect under conditions that allow for the expression and secretion of the polypeptide of interest;
- b) isolating the polypeptide of interest from the cell culture medium and
- c) optionally further processing the isolated polypeptide of interest.

According to a sixth aspect, the present disclosure pertains to the use of a polynucleotide encoding
- a) a mutated folate receptor comprising the following sequence

```
                                        (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNMKGWNWTSGFNKCAV

GAACQPFHFYFPTPTVLCNEIWTHSYKVSNYSRGSGRCIQMWFDPAQGN

PNEEVARFYA
``` wherein Xaa is not alanine and wherein the folate binding affinity of the mutated folate receptor is decreased compared to the corresponding wild type folate receptor wherein Xaa is alanine (SEQ ID NO 1),
or
- b) a mutated folate receptor comprising an amino acid sequence which has a sequence identity of at least 80%, at least 85%, at least 90%, at least 95%, at least 96%, at least 97%, at least 98% or at least 99% to the sequence shown as SEQ ID NO 9, and wherein Xaa is not alanine in said mutated folate receptor and wherein the folate binding affinity of said mutated folate receptor is decreased compared to the mature wild type human folate receptor alpha sequence wherein Xaa is alanine (see SEQ ID NO 1), as selectable marker for selecting cells, the viability of which is dependent on folate uptake.

According to a seventh aspect the present disclosure pertains to the use of a polynucleotide encoding
- a) a mutated folate receptor comprising the following sequence

```
                                        (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

VGAACQPFHFYFPTPTVLCNEIWTHSYKVSNYSRGSGRCIQMWFDPAQG

NPNEEVARFYA
``` wherein Xaa is leucine;
or
- b) a mutated folate receptor comprising an amino acid sequence which has a sequence identity of at least 80%, at least 85%, at least 90%, at least 95%, at least 96%, at least 97%, at least 98% or at least 99% to the sequence shown as SEQ ID NO 9 and wherein Xaa is leucine in said mutated folate receptor according to b), as selectable marker for selecting cells the viability of which is dependent on folate uptake. As is shown by the examples, a respective mutated folate receptor is a very efficient and stringent selectable marker, which also allows to select host cells expressing the respective selectable marker more rapidly than the wild type folate receptor.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only.

BRIEF DESCRIPTION OF THE FIGURES

FIG. 1: Single cell cloning of transfectants with V-DHFR-ref after selection (125 nM MTX)

FIG. 2: Single cell cloning of transfectants with V-DHFR-ref after selection (250 nM MTX)

FIG. 3: Single cell cloning of transfectants with V-wtFRalpha after selection (15 nM FA)

FIG. 4: Single cell cloning of transfectants with V-mutFRalpha (5 nM). As can be seen, more high expressing cell clones were obtained when using the mutated folate receptor as selectable marker compared to when using the wild type folate receptor as selectable marker. Furthermore, the expression rate was higher than observed with selection using DHFR as selectable marker.

FIG. 5: Single cell cloning of V-mutFRalpha/V-DHFRref co-transfected population (50 nM folic acid (FA)/50 nM MTX). As can be seen, significantly more and higher expressing cell clones were obtained when using such co-selection strategy.

DETAILED DESCRIPTION OF THE DISCLOSURE

Figure 1:
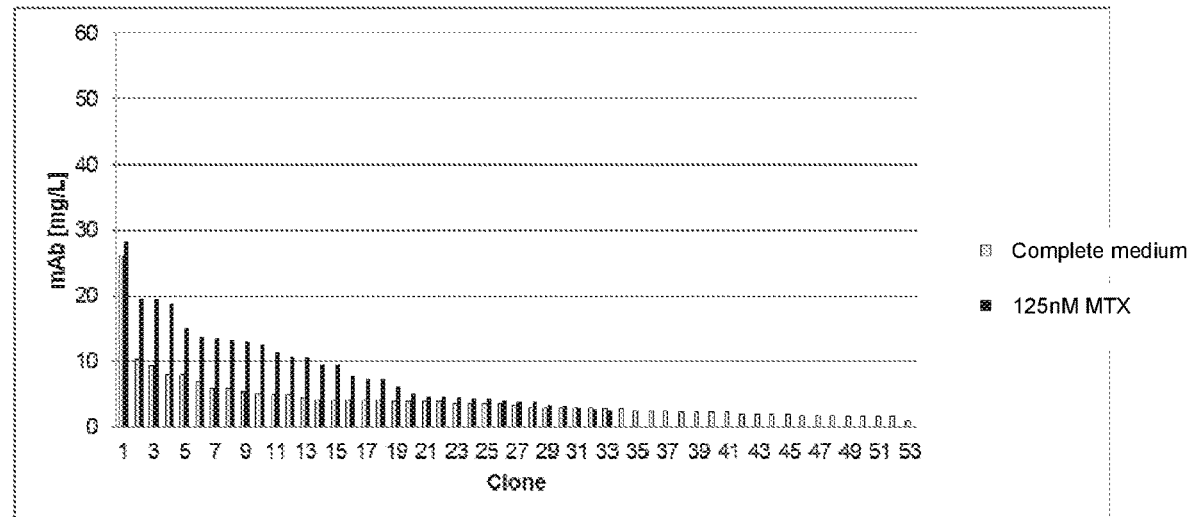
FIGS. 1 to 5 show the antibody productivities of individual cell clones that were obtained by limiting dilution from polyclonal cell pools that were beforehand transfected with different expression vectors and obtained using different selection conditions. Therefore, the productivity of clones obtained after selection is shown. For single cell cloning, the cells were either cultured in complete medium (thereby not maintaining the selection pressure after selection) or in selection medium (thereby maintaining the selection pressure after selection).
Figure 2:
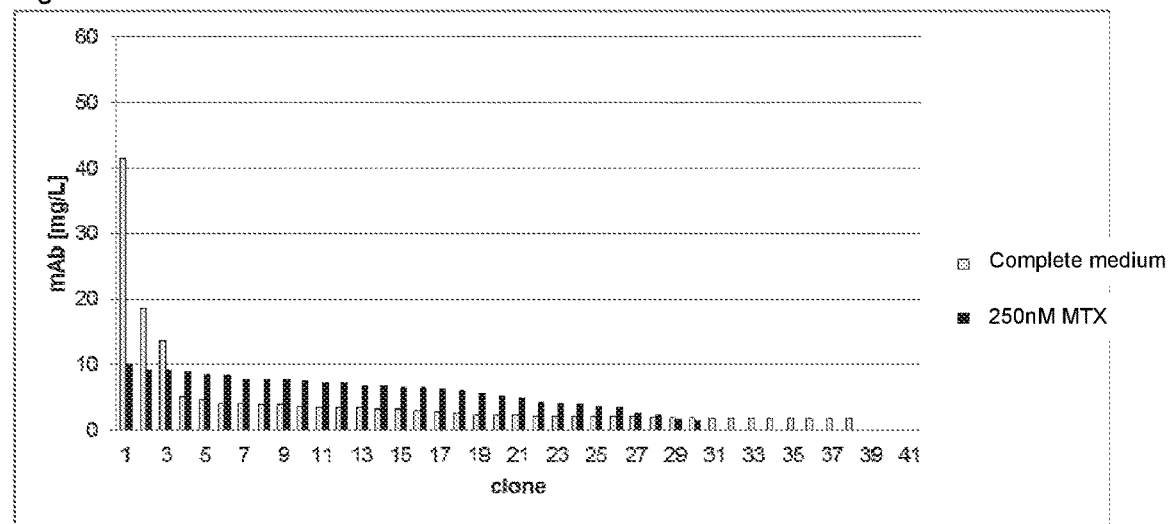
Figure 3:
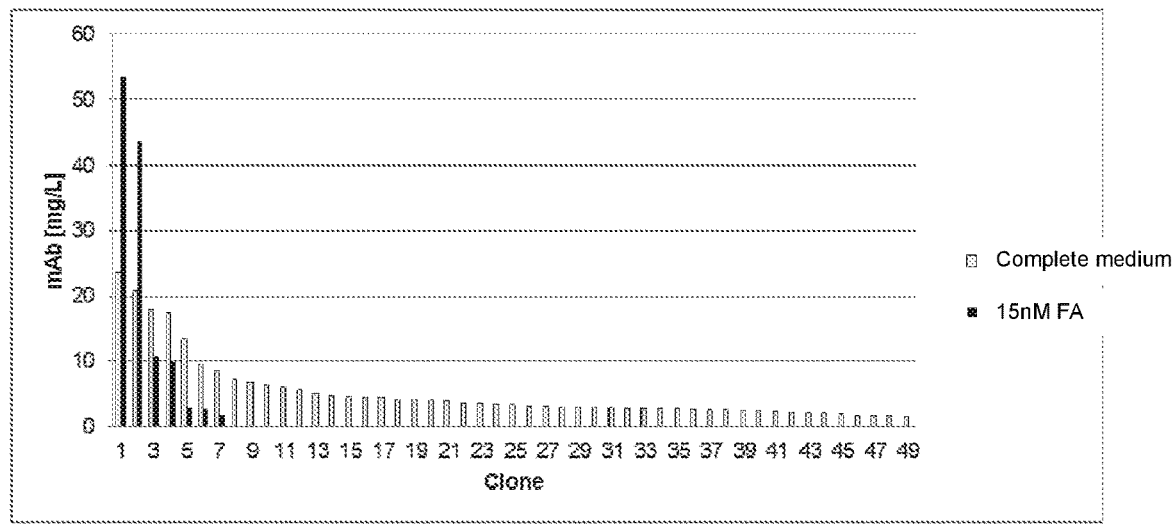
Figure 4:
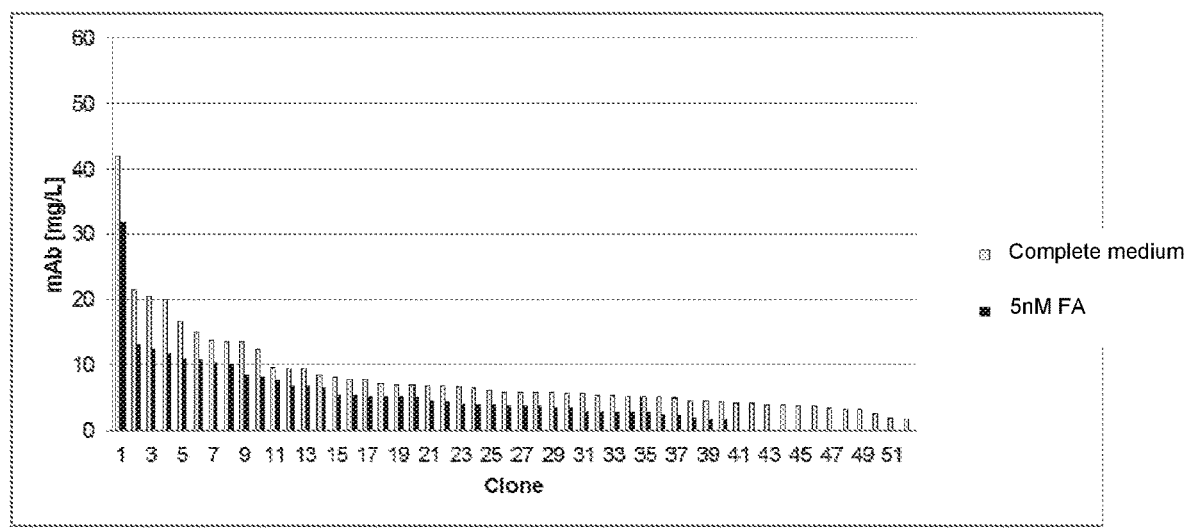

It was surprisingly found that a selection system that is based on the use of a folate receptor as selectable marker can be considerably improved by using a mutated form of a folate receptor. The mutated selectable marker can be used as dominant selectable marker for selecting eukaryotic cells, such as mammalian cells. Said mutant has a modulated folate binding affinity compared to the corresponding wild type folate receptor. It was found that a mutated folate receptor having a decreased folate binding affinity compared to the corresponding wild type folate receptor, has important advantages as selectable marker.

The novel system can be used for the accelerated selection, screening and establishment of eukaryotic, in particular mammalian, cell clones that stably express and secrete recombinant polypeptides with high yields. The selection can be performed using a culture medium that comprises a limiting concentration of folate, in particular a limiting concentration of folic acid. The novel selection system shows besides the general advantages that are associated with the use of a folate receptor as selectable marker several important advantages over selection systems available in the prior art and also over the use of the wild type folate receptor as selectable marker as will be explained in the following.

1. Improved rapidness and growth characteristics. As is shown in the examples, using a mutant folate receptor as selectable marker allows a considerably faster selection than standard selection systems that are based, e.g., on the use of DHFR as selectable marker. Furthermore, the selection system according to the present disclosure is also faster than a selection system that is based on the use of the wild type folate receptor as selectable marker. In particular, compared to the use of the wild type folate receptor as selectable marker, the cells which have incorporated the mutated folate receptor according to the present disclosure as selectable marker divide and recover faster when cultivated in a selective culture medium comprising very low folic acid concentrations. This achieved rapidness is a considerable advantage that reduces the length of a selection cycle. A respective growth advantage is observed even if very stringent selection conditions and accordingly highly limiting folic acid concentrations are used in the selective culture medium that even impair the growth of cells that were transfected with the wild type folate receptor as selectable marker. Thus, more stringent selection conditions can be used when using the mutated folate receptor according to the disclosure as selectable marker. This advantage of the mutated folate receptor according to the present disclosure over the wild type folate receptor was completely unexpected. Folate such as preferably folic acid must be present in the culture medium and must be efficiently incorporated into the host cells in order to sustain cell growth, purine and pyrimidine nucleotide biosynthesis, DNA replication and thus cellular proliferation. Considering this background, it was expected that cells transfected with a mutated folate receptor having a decreased folate binding affinity, would not have a growth advantage compared to cells that are transfected with the wild type folate receptor. It was even assumed that cells transfected with such mutant folate receptor as selectable marker might not even have a growth advantage compared to untransfected cells which endogenously express the wild type folate receptor having the full folate binding affinity. This particularly, as it was known that the expression of the endogenous folate receptor increases if untransfected cells are cultured in a culture medium comprising a limiting concentration of folate (see Zhu et al, Journal of Cellular Biochemistry 81:205-219 (2001)). Therefore, it was highly surprising when the inventors found that a mutated folate receptor which has a decreased folate binding affinity provides an efficient selectable marker which is even superior to the wild type folate receptor.

2. Improved stringency and productivity. Cells that have incorporated the mutated folate receptor according to the present disclosure as selectable marker surprisingly tolerate lower folate concentrations in the selective culture medium than cells comprising the wild type folate receptor as selectable marker. This allows to use more stringent selection conditions. Therefore, cells having a high productivity rate can be obtained faster when using the novel selectable marker described herein. This was completely unexpected considering the fact that the folate binding affinity of the mutated folate receptor according to the present disclosure is decreased compared to the wild type.

3. Improved reliability. A linear dose-dependency on the folate concentration in the culture medium is observed when using the mutated folate receptor according to the present disclosure as a selectable marker. The lower the folate concentration in the selection medium, the higher is the resulting productivity of the selected cells. A respective dependency is not observed in the same way when using the wild type folate receptor as selectable marker. This linear dose-dependency facilitates a more reliable control and optimization of the selection conditions. This finding was also completely unexpected.

Thus, the novel folate-based selection described herein which is based on the use of a mutated folate receptor as selectable marker which has compared to the corresponding wild type folate receptor a decreased folate binding affinity is an excellent strategy that is well-suited for the accelerated selection of stable cells which express a recombinant polypeptide of interest with high yield. The beneficial results described herein can be achieved at low folate concentrations in the cell culture medium and even in the absence of a cytotoxic drug selection as is routinely used in various other selection systems.

Expression vector and combination of expression vectors

According to a first aspect, the present disclosure provides an expression vector or a combination of at least two expression vectors comprising:

a) a polynucleotide encoding a mutated folate receptor as selectable marker, wherein the mutated folate receptor has a decreased folate binding affinity compared to the wild type folate receptor; and b) at least one polynucleotide encoding a polypeptide of interest, wherein when said expression vector or combination of at least two expression vectors is introduced into a host cell, the polypeptide of interest is secreted from said host cell.

A "vector" according to the present disclosure in particular refers to a polynucleotide capable of carrying at least one polynucleotide fragment. A vector functions like a molecular carrier, delivering polynucleotides into a host cell. An expression vector may comprise at least one expression cassette comprising regulatory sequences for properly expressing a polynucleotide incorporated therein. Polynucleotides (e.g. encoding the polypeptide of interest or a selectable marker) to be introduced into the cell may be inserted into the expression cassette(s) of the vector in order to be expressed therefrom. When introduced into a host cell, an expression cassette inter alia is capable of directing the cell's machinery to transcribe an incorporated polynucleotide encoding a polypeptide of interest into RNA, which is then usually further processed and finally translated into the polypeptide of interest. The vector may be present in circular or linear(ized) form. The term "vector" also comprises artificial chromosomes, viral vectors or similar respective polynucleotides allowing the transfer of foreign nucleic acid fragments.

A "polynucleotide" is a polymer of nucleotides which are usually linked from one deoxyribose or ribose to another and refers to DNA as well as RNA, depending on the context. The term "polynucleotide" does not comprise any size restrictions.

Subsequently, we describe embodiments of the expression vector and the combination of at least two expression vectors according to the present disclosure. The polynucleotide encoding the mutated folate receptor and the polynucleotide encoding a polypeptide of interest can be located on the same expression vector or on separate expression vectors if a combination of at least two expression vectors is used. If a combination of at least two expression vectors is used, wherein one expression vector comprises the polynucleotide encoding the polypeptide of interest and the other expression vector comprises the polynucleotide encoding the mutated folate receptor, said combination is co-transfected into the same host cells to enable selection. Respective co-transfection strategies are well known to the skilled person and are also described in the examples. Subsequently, we describe specific embodiments and advantages predominantly in conjunction with the embodiment wherein both polynucleotides are located on the same expression vector. However, said disclosure mutatis mutandis applies to the embodiment, wherein a combination of at least two expression vectors is used that are co-transfected into the cells. Where appropriate, we describe advantages associated with the expression vector or combination of at least two expression vectors in conjunction with the use of said expression vector(s) for selecting host cells expressing the polypeptide of interest with high yield.

Mutated Folate Receptor

A "folate receptor" as used herein refers to a receptor that is functional and thus capable of import or uptake of a folate or derivative thereof into a eukaryotic cell, in particular a mammalian cell. Preferably, the folate receptor is capable of unidirectional import or uptake of folate or derivative thereof into a eukaryotic host cell, in particular a mammalian cell. Furthermore, a folate receptor as used herein is membrane-bound. Thus, the folate receptors described herein are functional membrane-bound folate receptors. This applies to the mutated as well as the wild type folate receptor. Membrane anchorage can be achieved e.g. by a transmembrane anchor or a glycosylphosphatidylinositol (GPI) anchor. A GPI anchor is preferred as it corresponds to the natural setting of a folate receptor. Folate receptors (FRs) are high-affinity folate-binding glycoproteins. They are encoded by three distinct genes FR alpha, FR beta and FR gamma. FR alpha is also known as Adult Folate Binding Protein or FDP, as Folate Receptorl or FOLR (in mice folbpl), and as Ovarian cancer-Associated Antigen. FR beta is also known as FOLR2 (fetal) and as FBP/PL-1 (placenta). FR gamma is also known as FOLR3 and as FR-G (reviewed by M. D. Salazar and M. Ratnam, Cancer Metastasis Rev. 2007 26(1), pp. 141-152). The mature FRs, which are well-characterized, are homologous proteins with ~70-80% amino acid identity and contain 229 to 236 amino acids as well as two to three N-glycosylation sites. FR alpha and FR beta are membrane-bound proteins. FR alpha and FR beta are GPI-anchored, cell surface glycoproteins, whereas FR gamma is devoid of a GPI anchor and is a secreted protein. However, it can be genetically altered to include a transmembrane domain or a GPI anchor. Such an altered form of a FR gamma that includes a membrane anchor is also considered as wild type folate receptor if it is capable of import or uptake of a folate or derivative thereof into a eukaryotic cell as described before. FR alpha and FR beta display a high affinity for folic acid (Kd=0.1-1 nM), 5,10-dideazatetrahydrofolic acid (DDATHF; lometrexol; Ki=0.4-1.3 nM using [$^3$H]folic acid as a substrate) and BGC945 (which is a cyclopenta[g]quinazoline-based, thymidylate synthase inhibitor specifically transported solely via FRalpha and not via the reduced folate carrier) (Kd=1 nM), but much lower affinity for MTX (Kd>100 nM). FR-dependent uptake of folate and antifolates proceeds via a classical mechanism of receptor-mediated endocytosis.

A "mutated folate receptor having a decreased folate binding affinity compared to the wild type folate receptor" or similar expressions used herein in particular refer to a mutated folate receptor which compared to the corresponding wild type folate receptor has a reduced binding affinity to at least one folate selected from the group of reduced folates and oxidized folates. Said term in particular refers to mutated folate receptors which have compared to the corresponding wild type folate receptor a decreased folate binding affinity to a specific folate. The folate binding affinity to other folates i.e. folates different from said specific folate, may be unaltered. According to one embodiment, the mutated folate receptor having a decreased folate binding affinity comprises at least one mutation which compared to the corresponding wild type folate receptor decreases the binding affinity to at least one folate selected from the group of reduced folates and oxidized folates. According to one embodiment, the mutated folate receptor shows compared to the corresponding wild type folate receptor a decreased binding affinity to a reduced folate. According to one embodiment the mutated folate receptor shows compared to the corresponding wild type folate receptor a reduced binding affinity to the 6S diastereoisomer of 5-methyltetrahydrofolate. According to one embodiment, the mutated folate receptor has an $IC_{50}$ value for a reduced folate, preferably to the 6S diastereoisomer of 5-methyltetrahydrofolate, which is at least 20 fold, at least 30 fold, at least 40 fold, at least 50 fold or at least 55 fold higher than the $IC_{50}$ value of the corresponding wild type folate receptor. Due to the significantly higher $IC_{50}$ value it has a significantly reduced binding affinity to said reduced folate compared to the wild type folate receptor. According to one embodiment, the mutated folate receptor shows a reduced binding to folic acid.

The at least one mutation that results in a decreased folate binding affinity can be e.g. an amino acid substitution, deletion or insertion. According to one embodiment, the at least one mutation is present in the putative folate binding pocket. According to one embodiment, said mutation is a substitution in the putative folate binding pocket.

The mutated folate receptor that is used according to the present disclosure as selectable marker has a decreased folate binding affinity compared to the corresponding wild type folate receptor. As described above and as is shown by the examples, it is advantageous to use a mutated folate receptor which has compared to the corresponding wild type folate receptor at least a reduced binding affinity to the 6S diastereoisomer of 5-methyltetrahydrofolate. A decrease in the folate binding affinity can be achieved by introducing one or more mutations into the wild type sequence. Suitable examples are described below. Without being bound by theory, it is believed that due to the reduced folate binding affinity, cells transfected with the expression vector(s) according to the present disclosure need to express more of the mutated folate receptor to achieve a sufficient folate uptake rate in order to survive under selective folate deprivation conditions. Thus, also the polypeptide of interest is expressed at a higher level by the surviving population. As is shown by the examples, when using the mutated folate receptor as described herein as selectable marker, the productivity increases if the folate concentration in the selective culture medium is reduced. A respective correlation is not observed in the same way when using the wild type folate receptor as selectable marker. Furthermore, when using the mutated folate receptor as selectable marker, it is possible to even further reduce the folate concentration in the selective culture medium and hence to further increase the selection pressure on the transfected cells. Thereby, a very stringent and fast selection system is provided that is superior to a selection system which uses the wild type folate receptor as selectable marker. This was unexpected and highly surprising considering the fact that the folate binding affinity of the mutated folate receptor according to the present disclosure is decreased compared to the wild type folate receptor. Furthermore, it was surprisingly found that the cells that were transfected with the mutated folate transporter showed superior characteristics and in particular recovered earlier from the selection conditions, even when highly stringent selection conditions were used.

Preferably, the mutated folate receptor that is used as selectable marker comprises at least one mutation in the folate binding pocket wherein said mutation has the effect that the folate binding affinity is decreased compared to the corresponding wild type folate receptor. Suitable mutations are described subsequently. Incorporating a mutation in the folate binding pocket is a very efficient approach in order to reduce the folate binding affinity. Only cells that highly overexpress the introduced mutated folate receptor can incorporate sufficient amounts of folate from the culture medium to sustain cell growth, DNA replication and thus cellular proliferation. Surprisingly, even though the cells have incorporated a mutated folate receptor having a decreased affinity to folate as selectable marker, the transfected cells show a substantially accelerated growth compared to cells that were transfected with the wild type folate receptor or compared to cells that were transfected with a conventional selectable marker such as DHFR. This accelerated growth is a significant advantage as this reduces the time that is necessary for performing the selection.

The mutated folate receptor utilized according to the present disclosure can be derived from a folate receptor of any species as long as it will be functional within the present disclosure, i.e. it is compatible with the host cell that is utilized and when being expressed from the transfected host cell incorporates folate, in particular folic acid, from the culture medium into the host cell.

In general, the mutated folate receptor that is introduced into the eukaryotic host cell and utilized as selectable marker can be homologous or heterologous to an endogenous folate receptor of the host cell (if an endogenous folate receptor is present what is preferred). If it is homologous, it will be derived from the same species as the host cell. If it is heterologous, it will be derived from another species than the host cell. For example, a human-derived folate receptor may be used as selectable marker for a rodent host cell, e.g. a CHO cell. Preferably, a folate receptor derived from a mammalian species is used, for example derived from a rodent, such as mouse, rat or hamster, or, more preferred, derived from a human. According to one embodiment, a mutated folate receptor derived from human folate receptor alpha is used as selectable marker.

The mutated folate receptor can be selected from the group consisting of a folate receptor alpha, a folate receptor beta and a folate receptor gamma. The mutated folate receptor may be derived from a wild type folate receptor comprising an amino acid sequence as shown in SEQ ID NO 1, 3, 4, 6, 7 and 8 below, wherein, however, said mutated folate receptor comprises at least one mutation which results in a decreased folate binding affinity compared to the corresponding wild type folate receptor. Preferably, the mutated folate receptor is derived from a folate receptor alpha, in particular the human folate receptor alpha.

The mature wild type human folate receptor alpha comprises the following amino acid sequence (SEQ ID NO 1, 1-letter code, shown in direction from N-terminus to C-terminus):

IAWARTELLNVCMNAKHHKEKPGPEDKLHEQCRPWRKNACCSTNTSQEAH

KDVSYLYRFNWNHCGEMAPACKRHFIQDTCLYECSPNLGPWIQQVDQSWR

KERVLNVPLCKEDCEQWWEDCRTSYTCKSNMKGWNWTSGFNKCAVGAACQ

PFHFYFPTPTVLCNEIWTHSYKVSNYSRGSGRCIQMWFDPAQGNPNEEVA

RFYA

Folate receptor alpha is naturally anchored to the cell membrane by a GPI anchor. The signal sequence for a GPI anchor is not shown in SEQ ID NO 1. According to one embodiment, the mutated folate receptor alpha which is derived from SEQ ID NO 1 comprises a GPI anchor signal at the C-terminus. Any suitable GPI anchor signal may be used. The natural GPI anchor signal sequence of human folate receptor alpha is as follows (SEQ ID NO 2, 1-letter code, shown in direction from N-terminus to C-terminus):

AAMSGAGPWAAWPFLLSLALMLLWLLS

Membrane anchorage may alternatively be achieved by using a membrane anchor, e.g. a transmembrane anchor. In this embodiment, the mutated folate receptor comprises a membrane anchor at its C-terminus. Suitable anchors are known in the prior art.

The mutated folate receptor alpha which is derived from SEQ ID NO 1 may comprise a leader sequence at the N-terminus. Any suitable leader sequence can be used which ensures functional expression of the mutated folate receptor.

The full amino acid sequence including the natural leader sequence (at the N-terminus, underlined) and the natural GPI anchor signal sequence (at the C-terminus, underlined) of the wild type human folate receptor alpha is as follows (SEQ ID NO 3, 1-letter code, shown in direction from N-terminus to C-terminus):

MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHPYFPTPTVLCNEIWTHSYKVS

NYSRGSGRCIQMWFDPAQGNPNEEVARFYAAAMSGAGPWAAWPFLLSLAL

MLLWLLS

The wild type sequence of the mature human folate receptor beta has the following amino acid sequence (SEQ ID NO 4, 1-letter code, shown in direction from N-terminus to C-terminus):

QDRTDLLNVCMDAKHHKTKPGPEDKLHDQCSPWKKNACCTASTSQELHK

DTSRLYNFNWDHCGKMEPACKRHFIQDTCLYECSPNLGPWIQQVNQTWR

KERFLDVPLCKEDCQRWWEDCHTSHTCKSNWHRGWDWTSGVNKCPAGAL

CRTFESYFPTPAALCEGLWSHSYKVSNYSRGSGRCIQMWFDSAQGNPNE

EVARFYA

Folate receptor beta is naturally anchored to the membrane by a GPI anchor. The signal sequence for a GPI anchor is not shown in SEQ ID NO 4. According to one embodiment, the mutated folate receptor beta which is derived from SEQ ID NO 4 comprises a GPI anchor signal at the C-terminus. Any suitable GPI anchor signal may be used. The natural GPI anchor signal sequence of human folate receptor beta is as follows (SEQ ID NO 5, 1-letter code, shown in direction from N-terminus to C-terminus):

AAMHVNAGEMLHGTGGLLLSLALMLQLWLLG

Membrane anchorage may also be achieved by using a membrane anchor, e.g. a transmembrane anchor. In this embodiment, the mutated folate receptor comprises a membrane anchor at its C-terminus. Suitable anchors are known in the prior art.

The mutated folate receptor beta which is derived from SEQ ID NO 4 may comprise a leader sequence at the N-terminus. Any suitable leader sequence can be used which ensures functional expression of the mutated folate receptor.

The full amino acid sequence, including the leader sequence (at the N-terminus, underlined) and the natural GPI anchor signal sequence (at the C-terminus, underlined), of the wild type human folate receptor beta is as follows (SEQ ID NO 6, 1-letter code, shown in direction from N-terminus to C-terminus):

MVWKWMPLLLLLVCVATMCSAQDRTDLLNVCMDAKHHKTKPGPEDKLHDQ

CSPWKKNACCTASTSQELHKDTSRLYNFNWDHCGKMEPACKRHFIQDTCL

YECSPNLGPWIQQVNQTWRKERFLDVPLCKEDCQRWWEDCHTSHTCKSNW

HRGWDWTSGVNKCPAGALCRTFESYFPTPAALCEGLWSHSYKVSNYSRGS

GRCIQMWFDSAQGNPNEEVARFYAAAMHVNAGEMLHGTGGLLLSLALMLQ

LWLLG

Furthermore, a folate receptor can be used which is naturally not membrane-bound. Such a non-membrane bound folate receptor can be altered in order to become membrane-bound. For example a membrane anchor can be provided and said folate receptor can be expressed as a fusion protein comprising the folate receptor and a membrane anchor of another polypeptide. Furthermore, the sequence can be modified to incorporate a GPI anchor signal sequence. Suitable GPI anchor signal sequences were described above and are also known in the prior art. Thereby, the folate receptor can be anchored to the cell membrane by a GPI anchor. Likewise, other variants can be used which would be readily available for a person skilled in the art. Preferred examples in this respect would be a mutated folate receptor that is based on the folate receptor gamma, preferably the human folate receptor gamma, that was genetically altered to comprise a membrane anchor. Here, the folate receptor gamma sequence would be mutated according to the teachings of the present disclosure to show a decreased folate binding affinity.

The wild type human soluble folate receptor gamma has the following amino acid sequence (SEQ ID NO 7, 1-letter code, shown in direction from N-terminus to C-terminus):

QPRSARARTDLLNVCMNAKHHKTQPSPEDELYGQCSPWKKNACCTASTSQ

ELHKDTSRLYNFNWDHCGKMEPTCKRHFIQDSCLYECSPNLGPWIRQVNQ

SWRKERILNVPLCKEDCERWWEDCRTSYTCKSNWHKGWNWTSGINECPAG

ALCSTFESYFPTPAALCEGLWSHSFKVSNYSRGSGRCIQMWFDSAQGNPN

EEVAKFYAAAMNAGAPSRGIIDS

Furthermore, a mutated folate receptor gamma which is derived from SEQ ID NO 7 may comprise a leader sequence at the N-terminus. Any suitable leader sequence can be used which ensures functional expression of the mutated folate receptor.

The full amino acid sequence, including the leader sequence of the wild type human folate receptor gamma (underlined) is as follows (SEQ ID NO 8, 1-letter code, shown in direction from N-terminus to C-terminus):

MDMAWQMMQLLLLALVTAAGSAQPRSARARTDLLNVCMNAKHHKTQPSP

EDELYGQCSPWKKNACCTASTSQELHKDTSRLYNFNWDHCGKMEPTCKR

-continued

```
HFIQDSCLYECSPNLGPWIRQVNQSWRKERILNVPLCKEDCERWWEDCR

TSYTCKSNWHKGWNWTSGINECPAGALCSTFESYFPTPAALCEGLWSHS

FKVSNYSRGSGRCIQMWFDSAQGNPNEEVAKFYAAAMNAGAPSRGIIDS
```

A mutated folate receptor according to the present disclosure that is based on the folate receptor gamma comprises at least one mutation in the respective sequence to provide a mutated folate receptor having a reduced folate binding affinity. Preferably, the mutation is in the folate binding pocket.

According to one embodiment, the mutated folate receptor is derived from a folate receptor alpha or beta. According to one embodiment, a mutated folate receptor is obtained by providing a chimeric amino acid sequence that is derived from folate receptor alpha and beta. In folate receptor alpha and beta, important amino acid positions involved in ligand binding are, referring to the corresponding mature folate receptor amino acid sequence (see e.g. SEQ ID NO 1 and 4), positions 49, 104 and 166 (see also Ramamoorthy et al, 2007). According to one embodiment, the mutated folate receptor comprises at least one substitution in an amino acid position which corresponds structurally or by amino acid sequence homology to an amino acid position selected from position 49, 104 and 166 of the corresponding wild type sequence. Also more than one amino acid may be substituted in the mutated folate receptor in the respective positions. A substitution in one or more of these amino acid positions has a strong impact on the folate binding affinity. The substitution preferably decreases the folate binding affinity of the mutated folate receptor compared to the corresponding wild type folate receptor. According to one embodiment the resulting mutated folate receptor shows compared to the corresponding wild type folate receptor a reduced binding affinity to the 6S diastereoisomer of 5-methyltetrahydrofolate. According to on embodiment, the resulting mutated folate receptor shows a reduced binding to folic acid. According to one embodiment, the amino acid naturally occurring in the corresponding wild type sequence is substituted by a non-conservative amino acid, wherein said substitution decreases the folate binding affinity of the mutated folate receptor. According to one embodiment, the amino acid naturally occurring in the corresponding wild type sequence is substituted by a conservative amino acid. In a conservative exchange, an amino acid is replaced by another amino acid within a group with similar properties. Examples of corresponding groups are:

Amino acids having non-polar side chains: A, G, V, L, I, P, F, W, M

Uncharged amino acids having polar side chains: S, T, G, C, Y, N, Q

Amino acids having aromatic side chains: F, Y, W

Positively charged amino acids: K, R, H

Negatively charged amino acids: D, E

Amino acids of similar size or molecular weight, wherein the molecular weight of the replacing amino acids deviates by a maximum of +1-25% (or +1-20%, +1-15%, +1-10%) from the molecular weight of the original amino acid.

It is self-evident, that the groups also include modified amino acids and non-natural amino acids with the respective side chain profile such as e.g. homoarginine in case of the group depicting positively charged side chains. According to one embodiment, anamino acid naturally occurring in the wild type sequence is substituted by a natural L-amino acid in order to provide the mutated folate receptor.

Preferably, the mutated folate receptor is a folate receptor alpha. It can be derived from a rodent such as mouse, rat or hamster or can be derived from a human folate receptor alpha. Preferably, the mutated folate receptor is derived from a human folate receptor alpha. According to one embodiment, the mutated folate receptor according to the present disclosure is derived from the wild type human folate receptor alpha having the SEQ ID NO 1 or SEQ ID NO 3 shown above, wherein, however, said mutated folate receptor alpha comprises at least one mutation which results in a decreased folate binding affinity compared to the wild type folate receptor. According to one embodiment the resulting mutated folate receptor shows compared to the corresponding wild type folate receptor a reduced binding affinity to the 6S diastereoisomer of 5-methyltetrahydrofolate. According to on embodiment, the resulting mutated folate receptor shows alternatively or additionally a reduced binding affinity to folic acid.

Preferably, the mutated folate receptor according to the present disclosure comprises a substitution at the amino acid position which corresponds structurally or by amino acid sequence homology to amino acid 49 of the mature wild type human folate receptor alpha sequence as is shown in SEQ ID NO 1. A mutation in position 49 of the mature wild type sequence of folate receptor alpha introduces a mutation in the folate binding pocket and thus, has a strong impact on the folate binding affinity. This alanine in position 49 of the wild type sequence is found in the human as well as in the corresponding mouse wild type folate receptor alpha sequence. Of course, the mutated folate receptor according to the present disclosure may comprise additional mutations in other positions as long as the mutated folate receptor is functional. According to one embodiment, the at least one mutation which decreases the folate binding affinity compared to the wild type folate receptor is a substitution of the alanine present in position 49 of the mature wild type folate receptor alpha sequence by an amino acid selected from the group consisting of leucine, glycine, valine, isoleucine, histidine and aspartic acid. Preferably the alanine is substituted by leucine. The inventors surprisingly found that the substitution A49L in the sequence of the folate receptor alpha provides a mutated folate receptor alpha which has superior properties as selectable marker compared to the corresponding wild type folate receptor alpha. A mutated folate receptor alpha comprising a respective A49L substitution shows compared to the corresponding wild type folate receptor alpha a reduced binding affinity to a folate, namely the 6S diastereoisomer of 5-methyltetrahydrofolate. Furthermore, as is shown in the examples, the A49L mutant of the human folate receptor alpha shows significant advantages when being used as selection marker for identifying and selecting successfully transfected mammalian host cells. Therefore, it is preferably used as selection marker to identify host cells that express a recombinant polypeptide of interest with high yield.

According to one embodiment, the mature mutated folate receptor comprises an amino acid sequence which has a sequence identity of at least 80%, at least 85%, at least 90%, at least 95%, at least 96%, at least 97% or at least 98% or at least 99% to the mature wild type sequence of the human folate receptor alpha (SEQ ID NO 1), wherein, however, the amino acid sequence of the mature mutated folate receptor comprises at least one mutation which decreases the folate binding affinity compared to the wild type human folate receptor alpha. As discussed above, the at least one mutation which decreases the folate binding affinity compared to the wild type folate receptor preferably is a substitution of the alanine present in position 49 of the mature wild type folate receptor alpha sequence (see SEQ ID NO. 1) by an amino acid selected from the group consisting of leucine, glycine, valine, isoleucine, histidine and aspartic acid. Preferably, the alanine in position 49 is substituted by leucine. Such mutated folate receptor shows compared to the corresponding wild type folate receptor a reduced binding affinity to the 6S diastereoisomer of 5-methyltetrahydrofolate and improved characteristics as selectable marker.

According to one embodiment, the first polynucleotide encodes a mutated folate receptor, wherein said mutated folate receptor has the following characteristics:
a) the mature mutated folate receptor comprises the following sequence (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNMKGWNWTSGFNKCAV

GAACQPFHFYFPTPTVLCNEIWTHSYKVSNYSRGSGRCIQMWFDPAQGN

PNEEVARFYA wherein Xaa is not alanine and wherein preferably, Xaa is an amino acid selected from leucine, glycine, valine, isoleucine, histidine and aspartic acid and wherein more preferably Xaa is leucine;
or
b) the mature mutated folate receptor comprises an amino acid sequence which has a sequence identity of at least 80%, at least 85%, at least 90%, at least 95%, at least 96%, at least 97%, or 98% or at least 99% to the sequence shown as SEQ ID NO 9, and wherein Xaa is not alanine in said mutated folate receptor and preferably Xaa is an amino acid selected from leucine, glycine, valine, isoleucine, histidine and aspartic acid and more preferably Xaa is leucine and wherein the folate binding affinity of said mutated folate receptor is reduced compared to the mature wild type human folate receptor alpha sequence wherein Xaa is alanine (see SEQ ID NO 1). According to one embodiment, said mutated folate receptor shows compared to the corresponding wild type folate receptor a reduced binding affinity to the 6S diastereoisomer of 5-methyltetrahydrofolate. According to one embodiment, the resulting mutated folate receptor additionally or alternatively shows a reduced binding to folic acid. The mutated folate receptor according to b) can be seen as functional variant of a) and may comprise one or more amino acid additional mutation(s) compared to the mutated folate receptor according to a). E.g. it may comprise one or more additional substitutions, deletions and/or additions of one or more amino acids as long as the function as folate receptor is not eliminated. Also encompassed are fusion proteins, comprising a respective mutated folate receptor sequence.

As discussed above, preferably, Xaa is leucine. As is shown in the examples, mutating the alanine comprised in position 49 of the wild type sequence of the folate receptor alpha against leucine provides a mutated folate receptor which has compared to the corresponding wild type sequence superior characteristics as selectable marker. As is shown by the examples, cells comprising as selectable marker a mutated folate receptor carrying a mutation in the position corresponding to position 49 of the mature wild type sequence of the folate receptor alpha show after selection a high productivity of the polypeptide of interest which is often even considerably higher than the productivity that is achieved when using the corresponding wild type folate receptor as selectable marker and which is also higher than the productivity that is achieved with other mutated receptor forms. Furthermore, the cells recover faster from selection. These important advantages make the A49L mutated folate receptor particularly suitable as selectable marker. Said mutated folate receptor alpha was described and characterised in Shen et al, 1997. Therein, it was shown that said mutated version shows a reduced binding affinity to the 6S diastereoisomer of 5-methyltetrahydrofolate as can be seen by the $IC_{50}$ (nM) value that increases from the wild type folate receptor alpha (2.9) by almost 60-fold to (179.0).

The mutated folate receptor is membrane-bound and may comprise e.g. a GPI anchor or a transmembrane anchor. As described above, folate receptor alpha and beta are naturally anchored by a GPI anchor to the cell membrane. When using a GPI anchor for membrane anchorage, the encoding polynucleotide must provide the appropriate signal sequence for attaching a GPI anchor. Suitable signal sequences for the GPI anchor are known in the prior art and were also described above. As explained above, the respective GPI anchor signal sequences are provided at the C-terminal end and can be used in conjunction with the present disclosure.

According to one embodiment, the premature mutated folate receptor comprises the leader sequence of the wild type functional human folate receptor alpha as is shown in the following (SEQ ID NO 10, 1-letter code, shown in direction from N-terminus to C-terminus):

MAQRMTTQLLLLLVWVAVVGEAQTR

The leader sequences of the wild type human folate receptors beta and gamma are shown subsequently (SEQ ID NO 11 and 12, 1-letter code, shown in direction from N-terminus to C-terminus):

(SEQ ID NO 11)
MVWKWMPLLLLLVCVATMCSA (SEQ ID NO 12)
MDMAWQMMQLLLLALVTAAGSA

According to one embodiment, the first polynucleotide encodes a mutated folate receptor, wherein said mutated folate receptor has the following characteristics:
a) the mutated folate receptor comprises the following sequence (SEQ ID NO 13)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNMKGWNWTSGFNKCAV

GAACQPFHFYFPTPTVLCNEIWTHSYKVSNYSRGSGRCIQMWFDPAQGN

PNEEVARFYAAAMSGAGPWAAWPFLLSLALMLLWLLS wherein Xaa is leucine;
or
b) the mutated folate receptor comprises an amino acid sequence which has a sequence identity of at least 80%, at least 85%, at least 90%, at least 95%, at least 96%, at least 97%, at least 98% or at least 99% to the sequence shown as SEQ ID NO 13, wherein Xaa is leucine in said mutated folate receptor according to b) and wherein the binding affinity of said mutated folate receptor to the 6S diastereoisomer of 5-methyltetrahydrofolate is reduced compared to the mature wild type human folate receptor alpha sequence wherein Xaa is alanine (see SEQ ID NO 1).

The Polypeptide of Interest

The expression vector or combination of expression vector comprises at least one polynucleotide encoding a polypeptide of interest. When said expression vector or combination vector is introduced into a folate dependent host cell such as e.g. a mammalian cell as described herein, the polypeptide of interest is secreted from said host cell. Therefore, the polypeptide of interest is a secreted polypeptide. The polynucleotide may encode a polypeptide that is naturally secreted or it may be altered to become secreted by providing an appropriate secretory leader sequence. The majority of secreted polypeptides possess an amino-terminal leader peptide (also referred to as secretory leader sequence or signal peptide) that is cleaved from the nascent precursor polypeptide during biosynthesis. Secretory leader peptides are usually 5 to 60 amino acids long. This sequence is necessary and sufficient for secretion. Numerous examples of secretory leader sequences are well known in the prior art and thus, do not need any detailed description herein. Analysis of a large number of these secretory leader peptides has revealed a common structural motif that occurs in the absence of significant amino acid sequence homology [Von Heijne, 1981; Perlman et al, 1983, Bird et al, 1990]. In general, a secretory leader sequence consists of a positively charged amino terminus (n), a hydrophobic core (h) and a more polar carboxy terminus (c) that defines the signal peptidase cleavage site. Disruption of the h region by deletion or by replacement of hydrophobic residues with hydrophilic or charge amino acids leads to loss of signal function, whereas alterations to the "n" region have little effect. The carboxy terminus, or cleavage region, is typically about 6 amino acids long. This region is involved in signal peptidase recognition and cleavage, which is usually required to achieve final folding and secretion of the protein.

The polypeptide of interest can be a pharmaceutically or therapeutically active compound, or a research tool to be utilized in assays and the like. The polypeptide of interest can be of any kind. The term "polypeptide" refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity, function or size, and may include e.g. enzymes (e.g. proteases, kinases, phosphatases), receptors, transporters, bactericidal and/or endotoxin-binding proteins, structural polypeptides, glycoproteins, globular proteins, immune polypeptides, toxins, antibiotics, hormones, growth factors, blood factors, vaccines or the like. The polypeptide may be selected from the group consisting of peptide hormones, interleukins, tissue plasminogen activators, cytokines, immunoglobulins, in particular antibodies or functional antibody fragments or variants thereof and Fc-fusion proteins. The polypeptide of interest that is expressed according to the teachings described herein may also be a subunit or domain of a polypeptide, such as e.g. a heavy chain or a light chain of an antibody or a functional fragment or derivative thereof. The term "polypeptide of interest" may refer to such individual subunit or domain or the final protein that is composed of the respective subunits or domains, depending on the context. In a preferred embodiment the polypeptide of interest is an immunoglobulin molecule, more preferably an antibody, or a subunit or domain thereof such as e.g. the heavy or light chain of an antibody. The term "antibody" as used herein particularly refers to a protein comprising at least two heavy chains and two light chains connected by disulfide bonds. The term "antibody" includes naturally occurring antibodies as well as all recombinant forms of antibodies, e.g., humanized antibodies, fully human antibodies and chimeric antibodies. Each heavy chain is usually comprised of a heavy chain variable region (VH) and a heavy chain constant region (CH). Each light chain is usually comprised of a light chain variable region (VL) and a light chain constant region (CL). The term "antibody", however, also includes other types of antibodies such as single domain antibodies, heavy chain antibodies, i.e. antibodies only composed of one or more, in particular two heavy chains, and nanobodies, i.e. antibodies only composed of a single monomeric variable domain. As discussed above, the polynucleotide encoding the polypeptide of interest may also encode one or more subunits or domains of an antibody, e.g. a heavy or a light chain or a functional fragment or derivative thereof, as polypeptide of interest. Said subunits or domains can be expressed either from the same or different expression cassettes. A "functional fragment or derivative" of an antibody in particular refers to a polypeptide which is derived from an antibody and is capable of binding to the same antigen, in particular to the same epitope as the antibody. It has been shown that the antigen-binding function of an antibody can be executed by fragments of a full-length antibody or derivatives thereof. Examples of fragments or derivatives of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular.

Additional Selectable Markers

According to one embodiment, the expression vector or combination of at least two expression vectors according to the present disclosure additionally comprise(s) one or more polynucleotides encoding a further selectable marker. A selectable marker allows under appropriate selective culture conditions the selection of host cells expressing said selectable marker. A selectable marker provides the carrier of said marker under selective conditions with a survival and/or growth advantage. Typically, a selectable marker gene will confer resistance to a selection agent such as a drug, e.g. an antibiotic or other toxic agent, or compensate for a metabolic or catabolic defect in the host cell. It may be a positive or negative selection marker. For selecting successfully transfected host cells a culture medium may be used for culturing the host cells which comprises a selection agent that allows selection for the selectable marker used. In other embodiments, the selection marker enables the host cell to survive and proliferate in the absence or reduction of a compound which is essential for survival and/or proliferation of the host cells lacking the selection marker. According to one embodiment, the selectable marker is a drug resistance marker encoding a protein that confers resistance to selection conditions involving said drug. A variety of selectable marker genes is well-known to the skilled person and has been described in the literature (see, e.g., WO 92/08796, WO 94/28143, WO2004/081167, WO2009/080759, WO2010/097240). The selectable marker may according to one embodiment be an amplifiable selectable marker. Selectable marker genes commonly used with mammalian cells include the genes for aminoglycoside phosphotransferase (APH), hygromycin phosphotransferase (hyg), dihydrofolate reductase (DHFR), thymidine kinase (tk), glutamine synthetase, asparagine synthetase, and genes encoding resistance to neomycin (G418), puromycin, hygromycin and zeocin. Such selectable markers may be used in addition to the mutated folate receptor.

According to one embodiment, the expression vector or combination of expression vectors comprises an additional polynucleotide encoding a selectable marker that is involved in the folate metabolism and wherein the activity of said selectable marker is at least partially influenced by the activity of the mutated folate receptor. The feature, that the activity of the additional selectable marker is at least partially influenced by the activity of the mutated folate receptor particularly means that the activity of said additional selectable marker is influenced by and/or depends at least to a certain degree directly or indirectly on the activity or function of the mutated folate receptor. This dependency/interaction of the mutated folate receptor and the further selectable marker can be used to considerably increase the selection pressure on the host cells under selective culture conditions.

According to one embodiment the additional selectable marker is an enzyme which processes a substrate which is a folate, a derivative of folate and/or a product that can be obtained by the processing of folate such as DHF or THF or a functional variant or derivative of the foregoing. Respective substrates are important for the production of nucleic acids. Preferably, the additional selectable marker is a dihydrofolate reductase (DHFR) or an enzyme operating downstream of or in conjunction with DHFR such as thymidylate synthase (TS) and serine hydroxymethyltransferase (SHMT). Preferably, the additional selectable marker is a DHFR. DHFR may also be expressed as part of a fusion protein.

Using a respective combination of selectable markers, i.e. the mutated folate receptor according to the present disclosure and an additional selectable marker involved in the folate metabolism as described above, preferably DHFR, provides a very stringent selection system for obtaining and enriching high producing cells from the transfected host cell population. This concept of using a folate receptor as selectable marker in combination with a further selectable marker involved in the folate metabolism such as preferably DHFR and associated advantages is disclosed in WO 2010/097240, herein incorporated by reference. As is shown by the examples, the high stringency of the selection system according to this embodiment considerably lowers the number of low producers in the population obtained after selection and thereby increases the chance to find the very rare overproducing clones. Furthermore, a more homogenous population of high producing cells is obtained after selection what reduces the screening efforts. This simplifies single cell cloning of high producing cells. As is shown by the examples, using the mutated folate receptor as described herein in combination with an additional selectable marker involved in the folate metabolism as described above, preferably DHFR, results in improved results compared to when using the wild type folate receptor in combination with such selectable marker. Thus, also when using a combination of respective selectable markers, the present disclosure provides significant advantages due to the use of a mutated folate receptor.

As discussed above, the additional selectable marker preferably is a DHFR enzyme. Several suitable DHFR enzymes and accordingly genes are known in the prior art that can be used as selectable marker in conjunction with the present disclosure. The terms "dihydrofolatereductase" or "DHFR" refer to wild type DHFR as well as to DHFR enzymes having one or more amino acid sequence exchanges (e.g. deletions, substitutions or additions) with respect to the amino acid sequence of the corresponding wildtype DHFR enzyme, fusion proteins comprising a DHFR enzyme and DHFR enzymes which have been modified to provide an additional structure and/or function, as well as functional fragments of the foregoing, which still have at least one function of a DHFR enzyme. Such embodiments are well-known in the prior art and thus, do not need to be described in detail. For example, a DHFR enzyme may be used as selectable marker that is more or less sensitive to antifolates such as MTX than the wild type DHFR enzyme and/or the DHFR enzyme endogenously expressed by the host cell if expressed. Respective DHFR enzymes are well-known in the prior art and e.g. are described in EP 0 246 049 and other documents. The DHFR enzyme can be derived from any species as long as it will be functional within the present invention, i.e. compatible with the mammalian host cell utilised. E.g. a mutant mouse DHFR with a major resistance to MTX has been extensively used as a dominant selectable marker in mammalian cells. A DHFR enzyme may be used as selectable marker which is less susceptible to a DHFR inhibitor such as MTX than the DHFR enzyme endogenously expressed in a DHFR$^+$ (plus) host cell and thus a host cell which comprises a functional endogenous DHFR gene. According to one embodiment, an intron or a fragment thereof is placed at the 3' end of the open reading frame of the DHFR gene. The intron used in the DHFR expression cassette is leading to a smaller, non-functional variant of the DHFR gene (Grillari et al., 2001, J. Biotechnol. 87, 59-65). Thereby, the expression level of the DHFR gene is lowered which further increases the stringency of selection. Alternative methods making use of an intron to reduce the expression level of the DHFR gene are described in EPO 724 639 and could also be used.

The polynucleotide encoding the additional selectable marker can be located on the same expression vector as the polynucleotide encoding the mutated folate receptor and/or the at least one polynucleotide encoding the polypeptide of interest or it can be located on a separate expression vector if a combination of expression vectors is used. In this case the combination of expression vectors comprising all polynucleotides (encoding the mutated folate receptor, the polypeptide of interest and the additional selectable marker) would be co-transfected into the host cells to enable selection.

According to a preferred embodiment, the expression vector or combination of expression vectors comprises
 a polynucleotide encoding a mutated folate receptor which comprises at least one mutation corresponding structurally or by amino acid position to amino acid 49 of the mature wild type sequence of the human folate receptor alpha (see SEQ ID NO 1), wherein said mutation decreases the folate binding affinity compared to the wild type folate receptor alpha, wherein preferably, the alanine present in the wild type sequence in said position is substituted by leucine, and a polynucleotide encoding a DHFR that is less sensitive to MTX than the wild type DHFR enzyme and/or the DHFR enzyme endogenously expressed by the host cell as additional selectable marker. Said DHFR preferably also comprises an intron as is described above. A respective marker combination is particularly preferred if DHFR$^+$ (plus) cells are used as host cells. DHFR$^+$ (plus) cells express an endogenous DHFR. As is shown in the examples, very high producing cell clones can be efficiently selected when using a respective vector or combination of expression vectors.

The expression vector or combination of at least two expression vectors according to the present disclosure may additionally comprise one or more further polynucleotide(s) encoding a selectable marker. Such further selectable marker can be present in addition to the mutated folate receptor and the additional selectable marker involved in the folate metabolism, which preferably is DHFR.

Besides further eukaryotic selectable markers which allow the selection of eukaryotic host cells, also prokaryotic selectable markers can be present in the expression vector or combination of expression vectors. This e.g. allows the amplification of the vector(s) in prokaryotes. A "prokaryotic selectable marker" is a selectable marker allowing the selection in prokaryotic host cells under appropriate selection conditions. Examples of respective prokaryotic selectable markers are markers which provide a resistance to antibiotics such as e.g. ampicillin, kanamycin, tetracycline and/or chloramphenicol.

Further Vector Elements and Embodiments of the Expression Vector(s) The expression vector or the combination of at least two expression vectors can additionally comprise further vector elements. E.g. at least one additional polynucleotide encoding a further polypeptide of interest can be comprised. As explained above and as becomes apparent from the described examples of polypeptides that can be expressed, the final polypeptide that is to be produced and secreted by the host cell can also be a protein that is composed of several individual subunits or domains. A preferred example of a respective protein is an immunoglobulin molecule, in particular an antibody that comprises e.g. heavy and light chains. There are several options for producing a respective protein that is composed of different individual subunits or domains and appropriate vector designs are known in the art. According to one embodiment, two or more subunits or domains of said protein are expressed from one expression cassette. In this embodiment, one long transcript is obtained from the respective expression cassette that comprises the coding regions of the individual subunits or domains of the protein. According to one embodiment, at least one IRES element (internal ribosomal entry site) is functionally located between the coding regions of the individual subunits or domains and each coding region is preceded by a secretory leader sequence. Thereby, it is ensured that separate translation products are obtained from said transcript and that the final protein can be correctly assembled and secreted. Respective technologies are known in the prior art and thus, do not need any detailed description herein.

However, it is also within the scope of the present disclosure and for some embodiments such as the expression of antibodies it is even preferred to express the individual subunits or domains from different expression cassettes. According to one embodiment, the expression cassette used for expressing the polypeptide of interest is a monocistronic expression cassette. Preferably, all expression cassettes comprised in the expression vector or combination of expression vectors are monocistronic. According to one embodiment, accordingly, each expression cassette comprises a polynucleotide encoding one subunit or domain of the protein to be expressed as polypeptide of interest. For example, in case of antibodies, one expression cassette encodes the light chain of an antibody and another expression cassette encodes the heavy chain of the antibody. After expression of the individual subunits/domains from the individual expression cassettes, the final protein such as an antibody is assembled from said subunits or domains and secreted from the host cell. This embodiment is particularly suitable for expressing immunoglobulin molecules such as antibodies. In this case, a first polynucleotide encoding a polypeptide of interest encodes e.g. the heavy or the light chain of an immunoglobulin molecule and a second polynucleotide encoding a polypeptide of interest encodes the other chain of the immunoglobulin molecule. According to one embodiment, the expression vector or combination of at least two expression vectors comprises at least one expression cassette comprising a polynucleotide encoding the heavy chain of an immunoglobulin molecule or a functional fragment thereof and at least one expression cassette comprising a polynucleotide encoding the light chain of an immunoglobulin molecule or a functional fragment thereof. Said polynucleotides may be located on the same or on different expression vectors in case a combination of at least two expression vectors is used. Upon expression of said polynucleotides in the transfected host cell, a functional immunoglobulin molecule is obtained and is secreted from the host cell.

Expression vectors used for expressing recombinant products of interest usually contain as elements of an expression cassette transcriptional control elements suitable to drive transcription such as e.g. promoters, enhancers, polyadenylation signals, transcription pausing or termination signals as element of an expression cassette. Suitable translational control elements are preferably included, such as e.g. 5' untranslated regions leading to 5' cap structures suitable for recruiting ribosomes and stop codons to terminate the translation process. The resultant transcripts of the selectable marker gene(s) and that of the polypeptide of interest harbour functional translation elements that facilitate substantial levels of protein expression (i.e. translation) and proper translation termination. A functional expression unit, capable of properly driving the expression of an incorporated polynucleotide is also referred to as an "expression cassette" herein. The polynucleotide(s) encoding the polypeptide of interest to be secreted and the polynucleotides encoding the selectable marker(s) as described herein are preferably comprised in an expression cassette. Several embodiments are suitable, for example each of said polynucleotide(s) can be comprised in a separate expression cassette. However, at least two of the respective polynucleotides may also be comprised in one expression cassette. According to one embodiment, at least one internal ribosomal entry site (IRES) element is functionally located between the polynucleotides that are expressed from the same expression cassette. Thereby, it is ensured that separate translation products are obtained from said transcript. Respective IRES based expression technologies and other bi- and polycistronic sytsems are well known and thus need no further description here.

As described, the expression vector or combination of expression vectors according to the present disclosure may comprise at least one promoter and/or promoter/enhancer element as element of an expression cassette. Promoters can be divided in two classes, those that function constitutively and those that are regulated by induction or derepression. Both are suitable in conjunction with the present teachings. Promoters used for high-level production of proteins in mammalian cells should be strong and preferably active in a wide range of cell types. Strong constitutive promoters which drive expression in many cell types include but are not limited to the adenovirus major late promoter, the human cytomegalovirus immediate early promoter, the SV40 and Rous Sarcoma virus promoter, and the murine 3-phosphoglycerate kinase promoter, EF1a. According to one embodiment, the promoter and/or enhancer is either obtained from CMV and/or SV40. The transcription promoters can be selected from the group consisting of an SV40 promoter, a CMV promoter, an EF1alpha promoter, a RSV promoter, a BROAD3 promoter, a murine rosa 26 promoter, a pCEFL promoter and a δ-actin promoter.

According to one embodiment, the at least one polynucleotide encoding a polypeptide of interest, the polynucleotide encoding the mutated folate receptor and/or the polynucleotide encoding a second selectable marker are under the control of separate transcription promoters. The separate transcription promoters driving the expression from the polynucleotides can be the same or different.

According to one embodiment, a stronger promoter and/or enhancer is used for driving the expression of the at least one polynucleotide encoding the polypeptide of interest than for driving the expression of the polynucleotide encoding the mutated folate receptor and/or the one or more additional selectable markers. This arrangement has the effect that more transcript is generated for the polypeptide of interest than for the selectable markers. It is advantageous that the production of the polypeptide of interest is dominant over the production of the selectable markers, since the individual cell capacity for producing heterologous products is not unlimited and should thus be focused to the polypeptide of interest. Furthermore, the selection process only occurs at the initial stages of establishing an expression cell line, which then constantly produces the polypeptide of interest. Thus, it is advantageous to focus the resources of the cells to the expression/production of the polypeptide of interest. Furthermore, if a less strong promoter is used for expressing the selectable marker than is used for expressing the polypeptide of interest further increases the selection pressure on the transfected host cells.

According to one embodiment, the promoter driving the expression of the polynucleotide(s) encoding the polypeptide of interest is a CMV promoter and the promoter driving the expression of the polynucleotide encoding the mutated folate receptor is a SV40 promoter. The CMV promoter is known to be one of the strongest promoters available for mammalian expression and leads to a very good expression rate. It is considered to give significantly more transcript than the SV40 promoter. However, also other promoters can be used.

According to a further embodiment, the at least one polynucleotide encoding the polypeptide of interest and the polynucleotide encoding the mutated folate receptor and/or the polynucleotide encoding a selectable marker, if present, are under the control of the same transcription promoter. Suitable promoters are described above. In this embodiment, one long transcript is obtained from the respective expression cassette that is under the control of said transcription promoter. According to one embodiment, at least one IRES element is functionally located between the polynucleotides that are expressed from the same expression cassette.

The expression vector or combination of at least two expression vectors may comprise an appropriate transcription termination site as element of an expression cassette. This, as continued transcription from an upstream promoter through a second transcription unit may inhibit the function of the downstream promoter, a phenomenon known as promoter occlusion or transcriptional interference. Transcription termination sites are well characterized and their incorporation in expression vectors has been shown to have multiple beneficial effects on gene expression.

The expression cassettes may comprise a polyadenylation site. There are several efficient polyA signals that can be used in mammalian expression vectors, including those derived from bovine growth hormone (bgh), mouse beta-globin, the SV40 early transcription unit and the Herpes simplex virus thymidine kinase gene. However, also synthetic polyadenylation sites are known (see e.g. the pCl-neo expression vector of Promega which is based on Levitt el al, 1989, Genes Dev. 3, (7): 1019-1025). The polyadenylation site can be selected from the group consisting of SV40polyA site, such as the SV40 late and early poly-A site (see e.g. plasmid pSV2-DHFR as described in Subramani et al, 1981, Mol. Cell. Biol. 854-864), a synthetic polyA site (see e.g. the pCl-neo expression vector of Promega which is based on Levitt el al, 1989, Genes Dev. 3, (7): 1019-1025) and a bgh polyA site (bovine growth hormone).

Furthermore, an expression cassette may comprise at least one intron. Usually, introns are placed at the 5' end of the open reading frame but may also be placed at the 3' end.

Accordingly, an intron may be comprised in the expression cassette(s) to increase the expression rate. Said intron may be located between the promoter and or promoter/enhancer element(s) and the 5' end of the open reading frame of the polynucleotide to be expressed. Several suitable introns are known in the state of the art that can be used in conjunction with the present disclosure. According to one embodiment, the intron used in the expression cassettes for expressing the polypeptide of interest, is a synthetic intron such as the SIS or the RK intron. The RK intron consists of the intron donor splice site of the CMV promoter and the acceptor splice site of the mouse IgG Heavy chain variable region (see e.g. Eaton et al., 1986, Biochemistry 25, 8343-8347, Neuberger et al., 1983, EMBO J. 2(8), 1373-1378; it can be obtained from the pRK-5 vector (BD PharMingen)) and is preferably placed before the ATG start codon of the gene of interest.

The expression vector or vector combination according to the present disclosure can be transfected into the host cell in its circular form or in a linearized form. Linearization of the expression vector before transfection often improves the efficiency of a stable transfection. This also as the point of linearization may be controlled if the expression vector is linearized prior to transfection. Suitable designs for said linearization site are e.g. described in WO 2009/080720. The expression vector(s) may also comprise a prokaryotic origin of replication.

The expression vector or combination of expression vectors according to the present disclosure may comprise additional elements to allow the combination of the selection method according to the present disclosure which is based on the use of the mutated folate receptor with other selection systems known in the prior art.

One established selection method known in the prior art is based on the use of flow cytometry, in particular fluorescence activated cell sorting (FACS) in order to select high expressing host cells. Selection methods employing flow cytometry have the advantage that large numbers of cells can be screened rapidly for the desired characteristic expression yield. In one selection method that is particularly useful to identify high producing cell clones, a portion of the polypeptide of interest, e.g. an antibody, is expressed as membrane bound fusion polypeptide. Thereby, a portion of the product is displayed as fusion polypeptide on the cell surface. As the amount of produced fusion polypeptide correlates with the overall expression rate, the host cells can be selected via flow cytometry based upon the amount of fusion polypeptide displayed on the cell surface. This allows the rapid selection of high producing host cells. The selection system according to the present disclosure can be advantageously combined with respective selection methods that are based on the use of flow cytometry. To allow efficient selection using FACS, preferably a special expression cassette is used for expressing the polypeptide of interest. Thus, according to one embodiment, the polynucleotide encoding the polypeptide of interest is comprised in an expression cassette that is designed such that a portion of the expressed polypeptide of interest comprises a transmembrane anchor. Several options exist to achieve that result.

According to one embodiment, said expression cassette for expressing the polypeptide of interest comprises at least
  (i) the polynucleotide encoding the polypeptide of interest,
  (ii) at least one stop codon downstream of the polynucleotide encoding the polypeptide of interest, and
  (iii) a further polynucleotide downstream of the stop codon encoding a membrane anchor and/or a signal for a membrane anchor.

Transcription of the polynucleotide encoding the polypeptide of interest comprised in the above described expression cassette results in a transcript comprising in consecutive order at least
  (i) a polynucleotide, wherein translation of said polynucleotide results in the polypeptide of interest;
  (ii) at least one stop codon downstream of said polynucleotide;
  (iii) a polynucleotide downstream of said stop codon, encoding a membrane anchor and/or a signal for a membrane anchor.

A portion of the transcript is translated into a fusion polypeptide comprising the polypeptide of interest and the membrane anchor by translational read-through of the at least one stop codon. This design of the expression cassette has the effect that through translational read-through processes (the stop codon is "leaky") a portion of the polypeptide of interest is produced as a fusion polypeptide comprising a membrane anchor. The rest is expressed as secreted polypeptide of interest. The fusion polypeptide is displayed on the cell surface and cells displaying high levels of membrane-anchored fusion polypeptide can be selected by flow cytometry, preferably by FACS, e.g. using appropriate cell surface staining techniques. Thereby, host cells are selected that have a high expression rate. Details and preferred embodiments of this stop codon based technology are described in WO2005/073375 and WO2010/022961. It is referred to this disclosure.

According to one embodiment, the expression cassette additionally comprises (iv) a polynucleotide encoding a reporter, such as e.g. GFP. Said polynucleotide encoding the reporter is located downstream of the stop codon. Upon stop codon read-through a fusion polypeptide is obtained which comprises the reporter, thereby allowing selection by flow cytometry based on the characteristics of the expressed reporter such as e.g. its fluorescence. Preferably, the polynucleotide encoding the reporter is located downstream of the polynucleotide encoding a membrane anchor.

According to an alternative embodiment said expression cassette comprises at least
  (i) the polynucleotide encoding the polypeptide of interest,
  (ii) an intron comprising a 5' splice donor site and a 3' splice acceptor site and comprising an in frame translational stop codon and a polyadenylation signal and
  (iii) a polynucleotide downstream of said intron encoding a membrane anchor and/or a signal for a membrane anchor.

This design of the expression cassette has the effect that through transcription and transcript processing at least two different mature mRNAs (mRNA-POI) and (mRNA-POI-ANCHOR) are obtained from the expression cassette. Translation of the mRNA-POI results in the polypeptide of interest. Translation of the mRNA-POI-ANCHOR results in a fusion polypeptide comprising the polypeptide of interest (POI) and a membrane anchor. As a result, this fusion polypeptide is again displayed on the cell surface and cells displaying high levels of membrane-anchored fusion polypeptide can be selected by flow cytometry, preferably FACS. Thereby, host cells are selected that have a high expression rate. Details and preferred embodiments of this intron based technology are described in WO2007/131774. It is referred to this disclosure. According to one embodiment, the expression cassette additionally comprises (iv) a polynucleotide encoding a reporter, such as e.g. GFP. Said polynucleotide encoding the reporter is located downstream of the intron. Thereby, a fusion polypeptide is obtained which comprises the reporter, thereby allowing selection by flow cytometry based on the characteristics of the reporter such as e.g. its fluorescence. Preferably, the polynucleotide encoding the reporter is located downstream of the polynucleotide encoding a membrane anchor. Thereby, the reporter is located inside the host cell.

According to one embodiment, the expression cassette is constructed such that approximately ≤50%, 25%, ≤15%, ≤10%, ≤5%, ≤2.5%, ≤1.5%, ≤1% or less than ≤0.5% fusion polypeptide is obtained. The remaining portion is produced as the secreted polypeptide form not comprising the membrane anchor. The membrane anchor may be of any kind as long as it enables anchorage of the polypeptide of interest to the cell membrane and thus allows the display of the fusion polypeptide on the cell surface. Suitable embodiments include but are not limited to a GPI anchor or a transmembrane anchor. A transmembrane anchor is preferred to ensure tight binding of the fusion polypeptide to the cell surface and to avoid shedding of the fusion protein. Particularly preferred, in particular when expressing antibodies as polypeptide of interest, is the use of an immunoglobulin transmembrane anchor. Other membrane anchors and preferred embodiments of an immunoglobulin transmembrane anchor are described in WO2007/131774, WO2005/073375 and WO 2010/022961.

According to one embodiment, the polypeptide of interest is an immunoglobulin molecule such as an antibody. The polynucleotide encoding the heavy chain of an immunoglobulin molecule and the polynucleotide encoding the light chain of an immunoglobulin molecule may be comprised in the same expression cassette or preferably, are comprised in separate expression cassettes as was described above. When using an expression cassette design as described above, wherein a portion of the polypeptide of interest is produced as membrane-anchored fusion polypeptide by translational readthrough or alternative splicing, such expression cassette design is used for expressing the antibody heavy chain.

The Host Cells

According to a second aspect, the present disclosure provides a host cell the viability of which is dependent on folate uptake comprising at least a) an introduced polynucleotide encoding a mutated folate receptor which has a decreased folate binding affinity compared to the wild type folate receptor as selectable marker and b) an introduced polynucleotide encoding a polypeptide of interest, wherein said polypeptide of interest is secreted from said host cell.

An "introduced polynucleotide" refers to a polynucleotide sequence that has been introduced into a host cell e.g. by the use of recombinant techniques such as transfection. The host cell may or may not comprise an endogenous polynucleotide functionally corresponding to or being identical to the introduced polynucleotide. Preferably, introduction is achieved using an expression vector which comprises an expression cassette comprising the polynucleotide to be introduced, e.g. encoding the polypeptide of interest or encoding a mutated folate receptor. Preferred examples of expression vectors and combination of expression vectors according to the present disclosure were described above in conjunction with the first aspect of the present disclosure. Introduction may be achieved e.g. by transfecting a suitable expression vector that may integrate into the genome of the host cell (stable transfection). If the polynucleotide is not inserted into the genome, it can be lost at the later stage e.g. when the cells undergo mitosis (transient transfection). Suitable vectors might also be maintained in the host cell without integrating into the genome, e.g. by episomal replication. Stable transfection is preferred for generating high expressing cell clones that are suitable for producing a polypeptide of interest on industrial scale. There are several appropriate methods known in the prior art for introducing a polynucleotide such as an expression vector into eukaryotic host cells. Respective methods include but are not limited to calcium phosphate transfection, electroporation, nucleofection, lipofection, biolistic- and polymer-mediated genes transfer and the like. Besides traditional random integration based methods also recombination mediated approaches can be used to transfer the polynucleotide to be introduced into the host cell genome. As respective methods are well known in the prior art, they do not need any detailed description here. However, also other techniques are known in the prior art for introducing a polynucleotide into a host cell which are described in further detail below.

According to one embodiment, the host cell comprises an expression vector or combination of at least two expression vectors according to the first aspect which was described in detail above and in the claims. We refer to said disclosure which also applies here. Preferably, said expression vector or combination of expression vectors is stably integrated into the genome.

To allow selection with the system according to the present disclosure, the cellular viability of the host cell must be dependent on folate uptake, preferably on the uptake of folic acid. Suitable eukaryotic cells may be selected from the group consisting of mammalian cells, insect cells, yeast cells, plant cells and fungi cells. Fungi cells and plant cells can be prototrophic for folates (i.e. such cells can autonomously synthesize their own folates necessary for their cellular viability, i.e. cellular growth and proliferation). The present disclosure encompasses such fungi and plant cells which are or are rendered auxotrophic for folates. This may be for example due to genetic manipulation, i.e. cells are then unable to synthesize sufficient amounts of folates necessary for their cellular viability. Preferably, the host cell is a mammalian cell. All mammalian cells are dependent on folate uptake and accordingly can be used in conjunction with the selection system described herein. According to one embodiment, the mammalian cell is selected from the group consisting of a rodent cell, a human cell and a monkey cell. Particularly preferred is a rodent cell, which can be selected from the group consisting of a CHO cell, a BHK cell, a NS0 cell, a mouse 3T3 fibroblast cell, and a SP2/0 cell. A particularly preferred rodent cell is a CHO cell. Human cells can also be used and can be, selected from the group consisting of a HEK293 cell, a MCF-7 cell, a PerC6 cell, a CAP cell and a HeLa cell. Monkey cells can be selected from the group consisting of a COS-1, a COS-7 cell and a Vero cell.

According to one embodiment, the host cell is lacking the full activity of at least one endogenous folate receptor. Respective cell lines can be obtained through selection/screening processes or by genetic engineering techniques e.g. in order to generate knock-out cell lines. Thus, also a host cell is provided, wherein the endogenous unidirectional functional folate transport system, for example comprising at least one endogenous folate receptor, is lacking full activity, i.e. is attenuated. Such attenuation can be provided for example by any type of mutagenesis of the endogenous folate transport system in question, e.g. the endogenous folate receptor, for example by point mutation, gene disruption, and the like. The attenuation can be a partial or complete. In this case the host cell according to the present disclosure does not comprise an endogenous functional unidirectional functional folate transport system, e.g. an endogenous folate receptor.

According to a preferred embodiment, however, the host cell according to the present disclosure comprises at least one endogenous functional unidirectional functional folate transport system in addition to the mutated folate receptor that is introduced into said host cell e.g. via the expression vector or combination of expression vectors described above, in particular one or more endogenous folate receptor(s). Thus, genetically unaltered cells can be used for transfection with the expression vector or combination of expression vectors according to the present disclosure. It is an advantage of the present disclosure that the selection system described herein can be utilized even in the presence of such endogenous unidirectional functional folate transport system, i.e. where such endogenous system is retained. This is advantageous, as the use of the respective host cells for the subsequent production of the polypeptide of interest that occurs under non-selective conditions for folate is easier to handle if the endogenous system is retained and thus functional. As described above, mammalian host cells are preferred.

Accordingly, also a host cell is provided, comprising at least one endogenous unidirectional functional folate transport system, wherein such endogenous unidirectional functional folate transport system preferably comprises at least one endogenous folate receptor. In a preferred embodiment thereof, the endogenous folate receptor is selected from the group consisting of the folate receptor alpha and the folate receptor beta.

According to one embodiment, the host cell additionally comprises an introduced polynucleotide encoding an additional selectable marker which is involved in the folate metabolism. Embodiments were described above in conjunction with the first aspect and it is referred to the above disclosure. Preferably, said additional selectable marker is a DHFR. In conjunction with this embodiment, e.g. host cells (e.g. CHO cells) that lack the DHFR gene (e.g. by targeted genomic deletion, also called DHFR⁻ (minus) host cells) can be used as recipients for the co-transfection of the DHFR gene as selectable marker. However, it is also possible and preferred to use host cells that express DHFR endogenously (DHFR⁺ (plus) host cells) when performing a DHFR selection. In this case, preferably a DHFR enzyme is used as selectable marker which is less sensitive to MTX than the endogenous DHFR enzyme expressed by DHFR⁺ (plus) host cell.

According to one embodiment, the endogenous folate metabolism or machinery of the host cell is not genetically altered prior to introducing the polynucleotides by transfection.

The at least one polynucleotide encoding the polypeptide of interest, the polynucleotide encoding the mutated folate receptor and optionally the polynucleotide encoding the additional selectable marker involved in the folate metabolism (which preferably is DHFR) and optionally further polynucleotides as described above in conjunction with the first aspect may be stably introduced into said host cell. The stable introduction respectively transfection is advantageous for establishing expression cell lines and in particular for large scale production of a secreted polypeptide of interest, such as an antibody.

Method for Producing Recombinant Host Cells

According to a third aspect, a method for producing a host cell according to the second aspect is provided, comprising introducing into a host cell the viability of which is dependent on folate uptake at least
 a) a polynucleotide encoding a mutated folate receptor which has a decreased folate binding affinity compared to the wild type folate receptor as selectable marker and
 b) at least one polynucleotide encoding a polypeptide of interest, wherein the polypeptide of interest is secreted from said host cell.

There are several appropriate methods known in the prior art for introducing polynucleotides and expression vectors into a host cells, including eukaryotic host cells such as mammalian host cells. Respective methods are known in the prior art and were also described above. Besides traditional random integration based methods also recombination mediated approaches can be used to transfer the polynucleotide encoding the polypeptide of interest, the polynucleotide encoding the mutated folate receptor and optionally the polynucleotide encoding an additional selectable marker (and/or further polynucleotides) into the host cell genome. Such recombination methods may include use of site specific recombinases like Cre, Flp or ΦC31 (see e.g. Oumard et al, Cytotechnology (2006) 50: 93-108) which can mediate directed insertion of transgenes. Alternatively, the mechanism of homologous recombination might be used to insert said polynucleotides (reviewed in Sorrell et al, Biotechnology Advances 23 (2005) 431-469). Recombination based gene insertion allows to minimize the number of elements to be included in the heterologous nucleic acid that is transferred/introduced to the host cell. For example, an insertion locus might be used that already provides promoter and poly-A site (exogenous or endogenous) such that only the remaining elements need to be transferred/transfected to the host cell. Details regarding the polypeptide of interest, the mutated folate receptor and the one or more selectable markers (if used) as well as combinations thereof are described in detail above; we refer to the above disclosure. According to one embodiment, an expression vector or a combination of expression vectors according to the first aspect is introduced into the host cell. The expression vector and the combination of expression vectors is described in detail above and in the claims. It is referred to the respective disclosure. Furthermore, suitable examples of host cells the viability of which is dependent on folate uptake were also described above; it is referred to the respective disclosure.

Selection Method

According to a fourth aspect, the present disclosure provides a method for selecting at least one host cell capable of expressing a recombinant polypeptide of interest with high yield, comprising
 a) providing a plurality of host cells according to the second aspect of the present disclosure;
 b) culturing said plurality of host cells in a selective culture medium comprising a limiting concentration of folate;
 and
 c) obtaining at least one host cell expressing the polypeptide of interest.

The term "selecting" or "selection" as used herein, in particular refers to a process of using a selectable marker and selective culturing conditions to select and accordingly obtain host cells that have incorporated the polynucleotides to be introduced such as the expression vector or vector combination according to the present disclosure. Successfully transfected host cells can be obtained e.g. by isolation and/or enrichment from a population of transfected host cells. Successfully transfected host cells are capable of surviving the selection conditions and express the polypeptide of interest. The selection method is an ex vivo method.

A "limiting concentration of folate" as used herein in particular refers to a concentration of folate(s) in the selective culture medium which provides a selective pressure on the host cell. Accordingly, folates are not comprised in the selective culture medium in affluence, and this limitation of folate(s) in the culture medium provides a selection pressure on the host cells. Under such selection conditions, basically only host cells grow and/or proliferate that have incorporated the folate receptor as selectable marker. Host cells that have not successfully incorporated the polynucleotides to be introduced such as the expression vector or combination of at least two expression vectors and hence, do not express the mutated folate receptor as selectable marker or wherein expression is low cannot proliferate, grow and/or die under the selective culture conditions providing a limiting concentration of folate. In contrast, host cells that have successfully incorporated the expression vector or vector combination according to the present disclosure and which express the mutated folate receptor as selectable marker (and accordingly express the co-introduced polypeptide of interest) with sufficient yield are resistant to or are less affected by the selection pressure and therefore can during selection outgrow the host cells that were not successfully transfected or wherein the integration site into the genome of cell is not favourable in case of stable transfection.

The folate comprised in the selective culture medium in a limiting concentration is capable of being taken up into and being processed by the host cell, in particular by host cells that have incorporated the mutated folate receptor that is used as selectable marker. Folates and in particular derivatives of folate which would not or cannot be processed by the host cell do not contribute to the selection pressure that is exerted to select host cells that have incorporated the folate receptor as selectable marker and accordingly do not contribute to the limiting concentration of folate. However, respective folates, such as e.g. antifolates, may be present and even preferably are present, if e.g. a combined selection with DHFR as additional selectable marker is performed as described herein. The folate present in the selective culture medium in a limiting concentration can e.g. be an oxidized folate or a reduced folate or a derivative thereof. Oxidized folates, such as folic acid, as well as reduced derivatives of folic acid, known as reduced folates or tetrahydrofolates (THF), are a group of B9 vitamins that are essential cofactors and/or coenzymes for the biosynthesis of purines, thymidylate and certain amino acids in mammalian cells. Examples of reduced folates include 5-methyl-tetrahydrofolic acid, 5-formyl-tetrahydrofolic, 10-formyl-tetrahydrofolic acid and 5,10-methylene-tetrahydrofolic acid. In general, a folate is useful as long as such folate will be capable of being taken up into and processed by the host cell to maintain growth and proliferation. Preferably, the folate that is comprised in a limiting concentration in the selective culture medium is folic acid. Suitable concentration ranges for providing a limiting concentration of folate are described below.

During selection, host cells which have successfully incorporated the expression vector(s) according to the present disclosure can be enriched as pool from the population of transfected host cells. Such pool can then e.g. be analysed to identify comprised host cells that express the polypeptide of interest and e.g. have particular good expression rates, growth characteristics and/or stability properties. Also individual host cells can be isolated as single clones from the population of transfected and selected host cells (e.g. by clonal selection or FACS selection). Suitable embodiments of selection procedures in order to obtain successfully transfected single clones from the population of surviving host cells obtained after selection (e.g. by FACS sorting or limited dilution) are well known in the prior art and accordingly, need no detailed description.

Suitable and preferred embodiments of the host cells, the mutated selectable marker, additional selectable markers and marker combinations, expression vectors and vector combinations are described in detail above and it is referred to the above disclosure.

As described, the selection method according to the present disclosure is based on the limited availability of folate, preferably folic acid, in the cell culture medium. The system is widely applicable, and in particular can be used for selecting eukaryotic cells whose cellular viability depends on the uptake of folate, in particular folic acid, such as in particular mammalian cells. Examples of mammalian cells were described above. This folate-based selection in combination with the use of the mutated folate receptor as selectable marker is an excellent strategy that is well-suited for the accelerated, stable and high level overexpression of polypeptides in cultured mammalian cells. As is shown by the examples, the method according to the present disclosure, wherein a mutated folate receptor is used as selectable marker, allows an accelerated selection, screening and establishment of host cells, in particular mammalian host cells, that overexpress high levels of recombinant products such as antibodies. The results are improved over the use of a wild type folate receptor as selectable marker.

The selection system according to the present disclosure does as described above not require a genomic deletion or attenuation of the endogenous folate receptor gene(s) prior to transfection and thus can be applied to any recipient cell even if endogenous folate receptor gene expression is present. This key advantage is based upon the fact that following the transfection of the mutated folate receptor as selectable marker, cells can be exposed to an abrupt and severe deprivation of folates (e.g. folic acid) from the growth medium. Here, when using the mutated folate receptor having a lower folate binding affinity, even lower concentrations of folate can be used in the selective culture medium compared to a selection system that uses the wild type folate receptor. Only transfectant cells which express significant amounts of the mutated folate receptor as selectable marker can transport sufficient folate into the host cell to sustain DNA replication and cellular proliferation. This even occurs in the absence of any significant elevation in the expression of the endogenous folate receptor alpha gene during the selection cycle. Furthermore, the selection system according to the present disclosure apparently does not suffer from the loss of stringency of selection due to alleviation of the selective pressure via increased expression of alternative routes of folate uptake including increased expression of the endogenous RFC. This important advantage is due to the fact that whereas folate receptor alpha has an outstanding affinity for folic acid ($Kd=0.1$ nM), the RFC displays an extremely poor affinity for folic acid ($Km=0.2-0.4$ mM).

Cells obtained as a result of the stringent screening/selection procedure of the present disclosure can be isolated and enriched from non-selected cells of the original cell population. They can be isolated and cultured as individual cells or cell pools. The obtained host cells can also be used in one or more additional rounds of selection, optionally for additional qualitative or quantitative analysis, or can be used e. g. in development of a clonal cell line for protein production. According to one embodiment, an enriched population of producing host cells selected as described above is directly used as population for the production of the polypeptide of interest with a good yield.

Preferably, a host cell is selected which stably expresses and thus secretes the polypeptide of interest. The advantages of a stable transfection/expression are described in detail above. We refer to the above disclosure. Preferably, a clonal cell line is established from a selected host cell which expresses the protein of interest with the desired high yield.

The selective culture medium that is used in at least one selection step b) may comprise one or more types of folate. The folate comprised in the selective culture medium in a limiting concentration is capable of being taken up into and being processed by the transfected host cells to allow survival and preferably allow to sustain cell growth and proliferation. The selective culture medium that is used in step b) may have one or more of the following features:

(a) it comprises a limiting concentration of folate, wherein said folate is preferably folic acid, in a concentration selected from about 2000 nM or less, about 1750 nM or less, about 1500 nM or less, about 1000 nM or less, about 500 nM or less, about 350 nM or less, about 300 nM or less, about 250 nM or less, about 150 nM or less, about 100 nM or less, about 75 nM or less, about 50 nM or less, about 40 nM or less, about 35 nM or less, about 30 nM or less, about 25 nM or less, about 20 nM or less, about 15 nM or less, about 10 nM or less, about 5 nM or less and about 2.5 nM or less and; and/or (b) it comprises folic acid in a concentration selected from about 2000 nM or less, about 1750 nM or less, about 1500 nM or less, about 1000 nM or less, about 500 nM or less, about 100 nM or less, about 75 nM or less, about 50 nM or less, about 40 nM or less, about 35 nM or less, about 30 nM or less, about 25 nM or less, about 20 nM or less, about 15 nM or less, about 10 nM or less, about 5 nM or less and about 2.5 nM or less.

Preferred concentrations of folate and in particular folic acid in the selective culture medium may be selected from:

(a) about 2000 nM-0.1 nM;
(b) about 1750 nM-0.1 nM;
(c) about 1500 nM-0.1 nM;
(d) about 1250 nM-0.1 nM;
(e) about 1000 nM-0.1 nM;
(f) about 750 nM-0.1 nM;
(g) about 500 nM-0.1 nM;
(h) about 250 nM-0.1 nM; preferably about 250 nM-1 nM or about 250 nM-2.5 nM;
(i) about 150 nM-0.1 nM; preferably about 150 nM-1 nM or about 150 nM-2.5 nM;
(j) about 100 nM-0.5 nM; preferably about 100 nM-1 nM or about 100 nM-2.5 nM;
(k) about 75 nM-0.5 nM, preferably about 75 nM-1 nM or about 75 nM-2.5 nM;
(l) about 50 nM-1 nM; preferably about 50 nM-2.5 nM or about 50 nM-5 nM;
(m) about 35 nM-0.5 nM; and
(n) about 25 nM-1 nM or about 25 nM-2.5 nM, about 20 nM-3 nM about 15 nM-4 nM or
10 nM-5 nM.

According to one embodiment, folic acid is the only folate comprised in the selective culture medium that contributes to the limiting concentration of folate.

The concentrations and concentration ranges above described above are particularly suitable for fast growing suspension cells, such as CHO cells, which is a preferred phenotype for commercial production cell lines. The folate comprised in the selective culture medium is preferably folic acid. However, different cell lines may have different folic acid consumption properties. Suitable concentrations, however, can easily be determined experimentally by the skilled person. As is shown by the examples, using a mutated folate receptor as selectable marker allows to use lower folate concentrations in the selective culture medium.

According to one embodiment, the host cells are pre-cultured in a folate free culture medium or in a culture medium comprising a limiting concentration of folate prior to transfection and/or selection step b). Thereby, the cells are forced to use up their internal folate reservoirs. Suitable limiting concentrations of folate are described above. Preferably, said culture medium for pre-culturing the host cells comprises folate, in particular folic acid in a concentration of 100 nM or less, 75 nM or less, 50 nM or less, preferably 25 nM or less, more preferred 15 nM or less, most preferred 10 nM or less or can even be folate free. According to one embodiment, a cell bank, e.g. a master cell bank or a working call bank, is created from such host cells pre-cultured at limiting concentrations of folate, e.g. folic acid. This has the advantage of a shorter preparation time for transfection and cell line generation.

According to a preferred embodiment, the mutated folate receptor which is used as selectable marker according to the teachings of the present disclosure is used in combination with an additional selectable marker as described above. As discussed above, said additional selectable marker preferably is involved in the folate metabolism and preferably is a DHFR. According to one embodiment, wherein the cells are additionally transfected with a further selectable marker, the selective culture medium that is used in step b) comprises at least one suitable inhibitor for said additional selectable marker. The used concentration of said inhibitor in the selective culture medium (which may also be increased gradually), contributes to the stringency of the selection conditions. Furthermore, in order to maintain the selection pressure, the culture medium should not comprise sufficient amounts of metabolites that would allow to bypass the activity of the additional selectable marker. E.g. if DHFR is used as additional selectable marker that is involved in the folate metabolism it is advantageous that the selective culture medium does not comprise relevant nucleotides. In general, metabolites or other additives interfering with the chosen selection strategy shall be controlled, e.g. avoided in the selection medium.

The selection conditions for the mutated folate receptor (limiting concentration of folate) and for the additional selectable marker (e.g. a DHFR inhibitor if DHFR is used as selectable marker) can be applied simultaneously in step b) by using an appropriate selective culture medium. This increases the selective pressure and allows a more efficient selection procedure, thereby reducing the time for obtaining suitable cell lines expressing a polypeptide of interest with high yield. For the selectable marker combination mutated folate receptor/DHFR a selective culture medium is preferably used in step b) which comprises a limiting concentration of folate (suitable concentrations and examples of folate are described above) and which additionally comprises an inhibitor of DHFR, such as an antifolate. An inhibitor of DHFR in particular refers to a compound which inhibits the activity of the dihydrofolate reductase (DHFR). A respective inhibitor may for example compete with the DHFR substrate for binding to DHFR. Suitable DHFR inhibitors are for example antifolates such as methotrexate (MTX). Further examples include but are not limited to trimetrexate glucuronate (neutrexin), trimethoprim, pyrimethamine and pemetrexed. Thus, according to one embodiment, the selective culture medium used in step b) additionally comprises at least one DHFR inhibitor, such as preferably an antifolate such as MTX.

Thus, according to one embodiment, the host cells provided in step a) additionally comprise an introduced polynucleotide encoding a selectable marker which is a DHFR and in step b), a selective culture medium is used which comprises an antifolate in a concentration of 1500 nM or less, 1250 nM or less, 1000 nM or less, 750 nM or less, 500 nM or less, 250 nM or less, 200 nM or less, 150 nM or less, 125 nM or less, 100 nM or less or 75 nM or less. According to one embodiment, the selective culture medium comprises MTX as antifolate. Preferably, the selective culture medium comprises MTX in a concentration of about 350 nM or less, 200 nM or less, preferably about 150 nM or less, 125 nM or less, 100 nM or less, 75 nM or less or 50 nM or less. As is shown by the examples, it is a particular advantage that very low MTX concentrations can be used in conjunction with the method of the present disclosure. Preferred concentrations of antifolate and in particular MTX may be selected from:
(a) about 500 nM-1 nM;
(b) about 350 nM-2.5 nM;
(c) about 200 nM-5 nM;
(d) about 150 nM-7.5 nM;
(e) about 100 nM-10 nM; and
(f) about 75 nM-10 nM.

The preferred concentrations and concentration ranges for folate and antifolate described above can be combined with each other. In one embodiment, a folate concentration of about 0.1 nM-100 nM, preferably 1 nM-75 nM, more preferred 5 nM-50 nM is used in combination with an antifolate concentration of 2.5 nM-150 nM, preferably 5 nM to 125 nM, more preferred 7.5 nM to 100 nM, more preferably 10 nM to 50 nM in the selection culture medium. As described, preferably folic acid is used as folate and MTX as antifolate.

Furthermore, it was also found that the used folate and antifolate concentrations can influence each other. Thus, besides the absolute concentration of folates and antifolates, also the ratio can be a factor for providing suitable selection conditions. The concentration of antifolates (preferably MTX), can be up to about 20-fold of the folate (preferably folic acid) concentration. The antifolate (preferably MTX) concentration may be about 10-fold of the folate (preferably folic acid) concentration. Preferably, the selective culture medium comprises a folate and an antifolate in a concentration ratio of 1:10 to 10:1, preferably in a concentration ratio of 1:5 to 5:1. Very good results are obtained if approximately equimolar concentrations of folate and antifolate are used. As is shown by the examples, these ratios provide very suitable selective culture conditions to obtain high producing host cells if the desired combination of selectable markers is used.

This embodiment according to the present disclosure, wherein the mutated folate receptor is used in combination with a selectable marker involved in the folate metabolism, preferably DHFR, for selection has the advantage that the productivity of the cell population surviving selection is remarkably increased. In particular, the average productivity is remarkably increased as is shown by the examples if this principle is used in conjunction with the mutated folate receptor according to the present disclosure. The examples have shown that the host cells obtained after the selection method produce the polypeptide of interest with a particular high yield. Thus, chances are improved to find high producer clones with lower screening efforts. Thus, the selection system according to the present disclosure is superior to selection systems used in the prior art.

Furthermore, it was found that the productivity rates can even be further increased, if selection step b) is performed at least twice and wherein between each selection step b) the transfected cells are cultivated in a culture medium comprising non limiting or at least less limiting concentrations of folate and preferably no DHFR inhibitor and hence e.g. no antifolate. Therefore, between each selection step b) it is preferred to culture the cells under non-selective conditions. It was found that a respective repeated selection, wherein the cells are allowed to recover in between the selection steps or selection cycles, provides host cells that express the protein of interest with particular high yield and furthermore, the number of high producers was significantly increased.

As described above, one may also use one or more further selectable markers in addition to the mutated folate receptor and in addition to the selectable marker involved in the folate metabolism. The selective conditions for such further selectable marker can be applied prior to (e.g. in a pre-selection step which is performed inbetween steps a) and b)) or simultaneously with applying in step b) the selective conditions for the mutated folate receptor and optionally the selectable marker involved in the folate metabolism. E.g. in case the neomycin phosphotransferase gene (neo) is used as further selectable marker, the cells can be grown first in a medium e.g. containing G418 in order to pre-select cells that have incorporated the expression vector or the combination of at least two expression vectors according to the present disclosure. High expressing cells are then selected from said pre-selected cell population using the mutated folate receptor based selection, according to an advantageous embodiment in combination with a DHFR based selection.

Furthermore, as was described above, the selection method according to the present disclosure can be combined with flow cytometry based selection methods known in the prior art. Thus, according to one embodiment, a selection step involving flow cytometry is performed after the host cells were selected according to the method of the present disclosure and hence after step c). This can be done in order to select host cells from the surviving population which express the polypeptide of interest with a high yield. Such an approach makes manual cloning steps (e.g. limited dilution) obsolete. For this purpose, preferably at least a portion of the polypeptide of interest is expressed as a membrane anchored fusion polypeptide that is displayed on the cell surface of the host cell. Based on the amount of displayed fusion polypeptide, host cells can be selected using flow cytometry, preferably using FACS, which express the polypeptide of interest with high yield. Suitable expression cassettes for expressing the polynucleotide encoding the polypeptide of interest that allow a respective selection were described above. It is referred to the respective disclosure. For selection, the host cells are cultivated to allow the expression of the polypeptide of interest such that at least a portion of the polypeptide of interest is expressed as a fusion polypeptide comprising the membrane anchor, wherein said fusion polypeptide is being displayed on the surface of said host cell and wherein at least one host cell is selected based upon the amount of the fusion polypeptide displayed on the cell surface. Here, a labelled detection compound can be used which binds to the extracellular portion of the fusion protein. E.g. fluorescently labelled detection compounds may be used. Alternatively, the fusion protein may additionally comprise a reporter such as GFP, which marks the cell, thereby allowing direct selection based on the characteristics of the reporter. Preferably, the reporter is downstream of a transmembrane anchor and thus located intracellularly. As is discussed above, host cells can be selected for based on the expression yield using flow cytometry, in particular FACS.

Method for Producing a Polypeptide of Interest

According to a fifth aspect, a process is provided for producing a recombinant polypeptide of interest, comprising the step of culturing a host cell according to the present disclosure and/or a host cell selected according to the teachings of the present disclosure under conditions that allow for the expression and secretion of the polypeptide of interest. Using the host cells according to the present disclosure for producing a polypeptide of interest has the advantage that the polypeptide of interest can be produced with high yield. This particularly, when performing the selection method according to the present disclosure for selecting appropriate host cells for expression. Thus, the present disclosure provides an improved method for producing a polypeptide of interest. Suitable host cells are described above; we refer to the above disclosure.

The polypeptide is secreted into the culture medium and can be obtained therefrom. For this purpose, an appropriate secretory leader peptide is provided in the polypeptide of interest. Examples were described above Thereby, recombinant polypeptides can be produced and obtained/isolated efficiently with high yield. According to one embodiment, said host cells are cultured under serum-free conditions.

The method for producing the polypeptide of interest may comprise at least one of the following steps:
isolating the polypeptide of interest from said cell culture medium; and/or
processing the isolated polypeptide of interest.

The polypeptide of interest produced in accordance with the disclosure may also be subject to further processing steps such as e.g. purification and/or modification steps in order to produce the polypeptide of interest in the desired quality. For example, the product may be recovered from the nutrient medium by conventional procedures including, but not limited to, centrifugation, filtration, ultra-filtration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction. The isolated polypeptide of interest may be formulated as pharmaceutical composition.

Examples for the polypeptide of interest were described above in conjunction with the first aspect and it is referred to the respective disclosure. The mammalian cell may or may not comprise an endogenous polynucleotide corresponding to, respectively being identical to the polynucleotide encoding the polypeptide of interest. According to one embodiment, the mammalian cell does not comprise an endogenous gene corresponding to the polypeptide of interest. Also provided is a polypeptide obtained by a method according to the present disclosure as defined above and in the claims. Said polypeptide may in particular be an immunoglobulin molecule or a functional fragment thereof.

Uses

A sixth aspect of the present disclosure pertains to the use of a polynucleotide encoding
- a) a mutated folate receptor having or comprising the following sequence

```
                                                   (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNMKGWNWTSGFNKCAV

GAACQPFHFYFPTPTVLCNEIWTHSYKVSNYSRGSGRCIQMWFDPAQGN

PNEEVARFYA
``` wherein Xaa is not alanine and wherein the folate binding affinity of the mutated folate receptor is reduced compared to the corresponding wild type folate receptor wherein Xaa is alanine (SEQ ID NO 1)
  or
- b) a mutated folate receptor comprising an amino acid sequence which has a sequence identity of at least 80%, at least 85%, at least 90%, at least 95%, at least 96%, at least 97%, at least 98% or at least 99% to the sequence shown as SEQ ID NO 9, and wherein Xaa is not alanine in said mutated folate receptor and wherein the folate binding affinity of said mutated folate receptor is reduced compared to the wild type folate receptor alpha sequence wherein Xaa is alanine (see SEQ ID NO 1)

as selectable marker. Said selectable marker can be used for selecting successfully transfected host cells the viability of which is dependent on folate uptake such as in particular mammalian cells. In particular, it can be used as selection marker for identifying host cells expressing a recombinant polypeptide of interest with high yield. Preferably, said mutated folate receptor is comprised in an expression vector. Details, combinations and advantages of using a respectively mutated folate receptor as selectable marker and appropriate expression vectors were described above and it is referred to the above disclosure. In particular preferred is the use in the methods of the present disclosure. As described above, Xaa is preferably an amino acid selected from leucine, glycine, valine, isoleucine, histidine and aspartic acid. Most preferably Xaa is leucine. Preferably, the mutated folate receptor is GPI anchored. According to one embodiment said selectable marker is used in combination with DHFR as additional selectable marker. Details of this embodiment and appropriate selection condistions were described above and it is referred to the above disclosure.

A seventh aspect of the present disclosure pertains to the use of a polynucleotide encoding
- a) a mutated folate receptor comprising the following sequence

```
                                                   (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNMKGWNWTSGFNKCAV

GAACQPFHFYFPTPTVLCNEIWTHSYKVSNYSRGSGRCIQMWFDPAQGN

PNEEVARFYA
or
                                                  (SEQ ID NO 13)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNMKGWNWTSGFNKCAV

GAACQPFHFYFPTPTVLCNEIWTHSYKVSNYSRGSGRCIQMWFDPAQGN

PNEEVARFYAAAMSGAGPWAAWPFLLSLALMLLWLLS
``` wherein Xaa is leucine;
  or
- b) a mutated folate receptor comprising an amino acid sequence which has a sequence identity of at least 80%, at least 85%, at least 90%, at least 95%, at least 96%, at least 97% at least 98% or at least 99% to the sequence shown as SEQ ID NO 9 or SEQ ID NO 13 and wherein Xaa is leucine in said mutated folate receptor according to b), as selectable marker. Said selectable marker can be used for selecting cells the viability of which is dependent on folate uptake such as in particular mammalian cells. In particular it can be used as selection marker for identifying host cells expressing a recombinant polypeptide of interest with high yield. Preferably, said mutated folate receptor that is used as selectable marker is comprised in an expression vector. Details, combinations and advantages of using a respectively mutated folate receptor (A49L mutant) as selectable marker and of suitable and preferred expression vectors were described above and are also described in the examples. It is referred to the respective disclosure. In particular preferred is the use in the methods of the present disclosure. Preferably, the mutated folate receptor is GPI anchored. According to one embodiment said selectable marker is used in combination with DHFR as additional selectable marker. Details of this embodiment and appropriate selection conditions were described above and it is referred to the above disclosure. Preferred embodiments of this seventh aspect are again described in the following.

According to one embodiment of the seventh aspect, an expression vector or a combination of at least two expression vectors is used comprising:
- a) a polynucleotide encoding a mutated folate receptor as selectable marker wherein i) said mutated folate receptor comprises the following sequence (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

VGAACQPFHFYFPTPTVLCNEIWTHSYKVSNYSRGSGRCIQMWFDPAQG

NPNEEVARFYA
or (SEQ ID NO 13)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

VGAACQPFHFYFPTPTVLCNEIWTHSYKVSNYSRGSGRCIQMWFDPAQG

NPNEEVARFYAAAMSGAGPWAAWPFLLSLALMLLWLLS wherein Xaa is leucine;
or
ii) said mutated folate receptor comprises an amino acid sequence which has a sequence identity of at least 80%, at least 85%, at least 90%, at least 95%, at least 96%, at least 97%, at least 98% or at least 99% to the sequence shown as SEQ ID NO 9 or SEQ ID NO 13 and wherein Xaa is leucine in said mutated folate receptor according to ii)

b) at least one polynucleotide encoding a polypeptide of interest.

Preferably, the polynucleotide encoding the mutated folate receptor and the polynucleotide encoding the polypeptide of interest are comprised in separate expression cassettes. Details of suitable and preferred embodiments of expression cassettes and expression vectors were described above and it is referred to the above disclosure. Preferably, the polypeptide of interest is a secreted polypeptide. Details were described above in conjunction with the first aspect. According to one embodiment, the expression vector or combination of at least two expression vectors additionally comprises a polynucleotide encoding a selectable marker that is involved in the folate metabolism, preferably a dihydrofolate reductase. Suitable and preferred embodiments were described above and it is referred to the above disclosure. Said selectable marker which preferably is DHFR is preferably comprised in a separate expression cassette.

According to one embodiment of this aspect, also provided is a host cell the viability of which is dependent on folate uptake comprising
a) an introduced polynucleotide encoding a mutated folate receptor wherein
i) said mutated folate receptor comprises the following sequence (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

VGAACQPFHFYFPTPTVLCNEIWTHSYKVSNYSRGSGRCIQMWFDPAQG

NPNEEVARFYA
or (SEQ ID NO 13)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

VGAACQPFHFYFPTPTVLCNEIWTHSYKVSNYSRGSGRCIQMWFDPAQG

NPNEEVARFYAAAMSGAGPWAAWPFLLSLALMLLWLLS wherein Xaa is leucine;
or
ii) said mutated folate receptor comprises an amino acid sequence which has a sequence identity of at least 80%, at least 85%, at least 90%, at least 95%, at least 96%, at least 97%, at least 98% or at least 99% to the sequence shown as SEQ ID NO 9 or SEQ ID NO 13 and wherein Xaa is leucine in said mutated folate receptor according to ii) and b) at least one introduced polynucleotide encoding a polypeptide of interest, wherein the polypeptide of interest is secreted from said host cell.

Preferably, said host cell comprises an expression vector or combination of at least two expression vectors as described above. According to one embodiment the host cell is a mammalian cell. Preferably, it is a rodent cell, more preferably a CHO cell. According to one embodiment, the mammalian host cell expresses an endogenous folate receptor. According to one embodiment, the mammalian host cell comprises an introduced polynucleotide encoding a selectable marker involved in the folate metabolism, which preferably is a dihydrofolate reductase. Suitable and preferred embodiments were described in detail above as well as methods for producing a respective host cell. It is referred to the respective disclosure.

According to one embodiment of this aspect, also provided is a method for selecting at least one host cell capable of expressing a recombinant polypeptide of interest with a desired yield, comprising
a) providing a plurality of host cells the viability of which is dependent on folate uptake comprising
aa) an introduced polynucleotide encoding a mutated folate receptor wherein
i) said mutated folate receptor comprises the following sequence (SEQ ID NO 9)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

VGAACQPFHFYFPTPTVLCNEIWTHSYKVSNYSRGSGRCIQMWFDPAQG

NPNEEVARFYA
or (SEQ ID NO 13)
IAWARTELLNVCMNAKHHKEKPGPEDKLHEQCRPWRKNACCSTNTSQEX aaHKDVSYLYRFNWNHCGEMAPACKRHFIQDTCLYECSPNLGPWIQQVD

QSWRKERVLNVPLCKEDCEQWWEDCRTSYTCKSNWHKGWNWTSGFNKCA

-continued
VGAACQPFHFYFPTPTVLCNEIWTHSYKVSNYSRGSGRCIQMWFDPAQG

NPNEEVARFYAAAMSGAGPWAAWPFLLSLALMLLWLLS wherein Xaa is leucine;
or
ii) said mutated folate receptor comprises an amino acid sequence which has a sequence identity of at least 80%, at least 85%, at least 90%, at least 95%, at least 96%, at least 97%, at least 98% or at least 99% to the sequence shown as SEQ ID NO 9 or SEQ ID NO 13 and wherein Xaa is leucine in said mutated folate receptor according to ii) and
bb) at least one introduced polynucleotide encoding a polypeptide of interest;
b) culturing said plurality of host cells in a selective culture medium comprising folate in a limiting concentration;
and
c) obtaining at least one host cell expressing the polypeptide of interest.

The selective culture medium used in step b) comprises a limiting concentration of folate, wherein said folate is preferably folic acid, in a concentration selected from about 2000 nM or less, about 1750 nM or less, about 1500 nM or less, about 1000 nM or less, about 500 nM or less, about 350 nM or less, about 300 nM or less, about 250 nM or less, about 150 nM or less, about 100 nM or less, about 75 nM or less, about 50 nM or less, about 40 nM or less, about 35 nM or less, about 30 nM or less, about 25 nM or less, about 20 nM or less, about 15 nM or less, about 10 nM or less, about 7.5 or less, about 5 nM or less and about 2.5 nM or less. Preferably, folic acid is used as folate. The host cell preferably is a mammalian cell. According to one embodiment, the host cell additionally comprises an introduced polynucleotide encoding a selectable marker which is a dihydrofolate reductase. In this embodiment, the selective culture medium used in step b) additionally comprises according to one embodiment an antifolate in a concentration selected from 1500 nM or less, 1000 nM or less, 750 nM or less, 500 nM or less, 200 nM or less, 150 nM or less, 125 nM or less, 100 nM or less, 75 nM or less, 50 nM or less, 25 nM or less, 20 nM or less, 15 nM or less, 12 mM or less and 10 nM or less. According to one embodiment, after step c), the cells are cultured in a culture medium comprising a non-limiting concentration of folate and are then again cultured according to step b) and obtained according to step c). Further details of preferred and suitable selective culture media and embodiments of the selection method were described above in conjunction with the fourth aspect and it is referred to the respective disclosure.

According to a further embodiment of this aspect, also provided is a process for producing a polypeptide of interest, comprising
a) culturing a host cell as described in the preceeding paragraphs of this aspect and/or a host cell selected according to the method described in the preceeding paragraphs of this aspect under conditions that allow for the expression and secretion of the polypeptide of interest;
b) isolating the polypeptide of interest from the cell culture medium and
c) optionally processing the isolated polypeptide of interest.

Details regarding a respective production method, as well suitable and preferred embodiments of the polypeptide of interest were also described above and it is referred to the above disclosure. Preferably, the polypeptide of interest is a therapeutically active polypeptide such as an antibody.

This invention is not limited by the exemplary methods and materials disclosed herein. Numeric ranges described herein are inclusive of the numbers defining the range. The headings provided herein are not limitations of the various aspects or embodiments of this invention which can be read by reference to the specification as a whole. According to one embodiment, subject-matter described herein as comprising certain elements also refers to subject-matter consisting of the respective elements. In particular, the polynucleotides described herein as comprising certain sequences may also consist of the respective sequences. It is preferred to select and combine preferred embodiments described herein and the specific subject-matter arising from a respective combination of preferred embodiments also belongs to the present disclosure.

The following examples serve to illustrate the present disclosure without in any way limiting the scope thereof. In particular, the examples relate to preferred embodiments of the present disclosure.

EXAMPLES

In the subsequent experiments, the following vectors were used:

The reference vector "V-DHFRref" comprised the following main expression cassettes: An expression cassette comprising a polynucleotide encoding DHFR as selection marker; an expression cassette comprising a polynucleotide encoding the light chain of an antibody; an expression cassette comprising a polynucleotide encoding the heavy chain of an antibody and an expression cassette comprising a polynucleotide encoding a neomycin phosphotransferase. All expression cassettes were oriented in the same direction. A full antibody is expressed from said reference vector. A suitable vector design is also described in WO 2009/080720.

The vectors comprising a folate receptor as selection marker were designed based on the reference vector by exchanging the polynucleotide encoding DHFR as selectable marker against a polynucleotide encoding a folate receptor as selectable marker. Otherwise, the expression cassettes remained the same. The vector "V-wtFRalpha" comprised the wild type human folate receptor alpha as selection marker. The vector "V-mutFRalpha" comprised the mutant human folate receptor alpha comprising the A49L mutation.

Example 1

Single Transfections

For single transfections, the wild type human folic acid receptor alpha (vector: V-wtFRalpha) or a mutant human folate receptor alpha (vector: V-mutFRalpha) were introduced as selection marker into CHO cells. This experiment served the purpose to analyze the function of the folate receptor selection system, which in contrast to the DHFR/MTX-system is not based on a toxic inhibition of cell growth, but is based on a growth inhibition due to folic acid deprivation in the culture medium. Folic acid is the oxidized form of vitamin B9. Folic acid is biologically active in its reduced form, tetrahydrofolate (THF). Folic acid is reduced in the cell into its biologically active form tetrahydrofolate (THF) via dihydrofolate (DHF) in an NADPH-dependent reaction by the enzyme dihydrofolate reductase (DHFR). The uptake of folic acid is essential for mammalian cells in order to sustain cell growth and cell proliferation.

Only cells that integrate the transfected vector into the genome and express either the wild type folate receptor alpha (V-wtFRalpha) or the mutated folate receptor alpha (V-mutFRalpha) with high efficiency can survive the selection conditions that are based on a limiting concentration of folate in the culture medium. These cells are able to incorporate a sufficient amount of folic acid from the culture medium into the cells in order to sustain proliferation in cell growth even though the culture medium comprises a limiting concentration of folic acid. Because the expression vectors also introduce polynucleotides encoding a protein of interest (in these experiments the heavy and the light chain of an antibody) into the cells, it is possible to select stable, high producing production cell lines using the folate receptor based selection technology.

In order to determine the influence of the folic acid concentration on the growth of the cells, different selective culture media were tested. The standard culture medium comprises 11.7 µM folic acid (complete medium). It was found, that most stringent selection conditions were achieved when using 50 nM folic acid in the culture medium. Furthermore, differences in the growth rates were observed when using different folic acid concentrations. The less folic acid in the culture medium, the slower was the growth of the cells.

First, the internal folic acid reservoirs of the CHO cells were reduced and a co-transfer from folic acid from the standard cultivation medium (complete medium) into the selection medium was prevented. Therefore, prior to transfection, the cells intended for selection with a limiting folic acid concentration were washed three times with PBS and were inoculated in folic acid free medium. The reference control (vector V-DHFRref) was passaged with the same cell density in complete medium. The growth of the cells was analyzed prior to transfection and it was found, that the culture that was grown in complete medium ($5 \times 10^6$ LZ/ml) grew approx. 2 times better than the culture that was grown in selection medium ($2.5 \times 10^6$ LZ/ml).

The vectors were transfected into the cells using nucleofection. $5 \times 10^6$ vital cells (LZ/ml) were transfected with 3 µg vector DNA. CHO cells comprising the vectors V-wtFRalpha, V-mutFRalpha and the negative controls (V-DHFRref and without DNA) were transferred into the selection medium; the reference transfections were transferred into complete medium. The performed single transfections are summarized in Table 1. Selection began 48 hours after transfection, thereby allowing the cells to recover from nucleofection and to start the expression of the introduced expression vectors. The cells comprising the selection markers to be tested were exposed to limited concentrations of folic acid. In parallel, the selection marker DHFR (V-DHFRref) was exposed to different MTX comprising culture media as well as to different folic acid (FA) containing selection media. A culture without additional DNA served as negative control.

TABLE 1

Overview over the performed single transfections

| Transfection | Vector | Meaning | Medium before/after transfection | Selection medium after 48 h |
|---|---|---|---|---|
| 1-4 | V-DHFRref | reference control | complete medium | 2 µM, 1 µM, 500 nM, 250 nM or 125 nM MTX, complete medium |
| 5-8 | V-DHFRref | negative control | selective medium | 50 nM, 45 nM, 35 nM, 25 nM, 15 nM or 5 nM FA |
| 9-12 | without DNA | negative control | selective medium | 50 nM, 45 nM, 35 nM, 25 nM, 15 nM or 5 nM FA |
| 13-16 | V-wtFRalpha | FRalpha wild type | selective medium | 50 nM, 45 nM, 35 nM, 25 nM, 15 nM or 5 nM FA |
| 17-20 | V-mutFRalpha | FRalpha mutant | selective medium | 50 nM, 45 nM, 35 nM, 25 nM, 15 nM or 5 nM FA |

The transfection efficiency was determined after 48 h via a GFP control. Subsequent Table 2 provides an overview over the achieved viable cell density at day 12 of the folic acid based selection.

TABLE 2

Overview over the cell density (LZ/mL) at day 12 of the folic acid (FA) based selection

| | Without DNA | V-DHFRref (DHFR) | V-wtFRalpha (FRα) | V-mutFRalpha (FRα*) |
|---|---|---|---|---|
| 50 nM FA | 2.10E+06 | 1.74E+06 | 2.34E+06 | 4.37E+06 |
| 45 nM FA | 1.66E+06 | 1.58E+06 | 1.44E+06 | 3.31E+06 |
| 35 nM FA | 1.06E+06 | 9.53E+05 | 7.29E+05 | 2.39E+06 |
| 25 nM FA | 2.55E+05 | 1.66E+05 | 2.38E+05 | 6.75E+05 |
| 15 nM FA | 1.09E+05 | 1.39E+05 | 2.72E+05 | 7.57E+05 |
| 5 nM FA | 1.02E+04 | 3.73E+04 | 3.73E+04 | 3.63E+05 |

Table 2 shows the cell density [LZ/mL] of the cell pools transfected with the controls (V-DHFRref; without DNA), V-wtFRalpha and V-mutFRalpha and selected using different folic acid concentrations. As can be seen, the growth is reduced when the folic acid concentration in the selection medium is reduced. Cell pools that were transfected with the mutated folate receptor alpha as selection marker show in the selection media comprising limiting concentrations of folic acid a cell growth, which is approximately twice as high or even higher as the cell growth that is observed in the other pools. At day 12, the cells transfected with the wild type folate receptor alpha did not yet show a growth advantage. They grew approximately equally well as the populations comprising V-DHFRref or the negative controls. However, a growth advantage is seen with the with type folate receptor alpha at a later stage beginning—depending on the used folic acid concentration—approx. at day 16 to 20. Thus, both types of folate receptors (wild type and mutant) are suitable for selecting cells based on a limiting concentration of folic acid in the culture medium. However, the use of a mutated folate receptor alpha as selectable marker as taught by the present disclosure is more advantageous because a growth advantage of successfully transfected cells is seen earlier than with the wild type folate receptor alpha. Furthermore, the mutated folate receptor allowed a selection at lower folic acid concentrations, such as 15 nM and even 5 nM. Thus, more stringent selection conditions can be used when using a mutated folate receptor according to the disclosure as selection marker.

When analyzing the viability of the cell pools at day 12 of selection, the observed viability was approximately the same at folic acid concentrations of 35-50 nM (viability of the cell pools >90%). Due to the high viability it was possible to passage the populations at this day. However, at lower folic acid concentrations the viability was reduced. In the lowest folic acid selective media, only the V-mutFRalpha transfected population showed a relatively high viability of 76%.

Furthermore, the time necessary for selection was analysed. The overall time that is needed for selection is important when establishing a new selection marker. When cultivating CHO cells, a single selection step DHFR-MTX-selection may be completed depending on the used selection conditions within 15 to 16 days. Multistep gene amplification, however, usually takes significantly longer. During this time period, the cells should recover from the crisis that is induced due to the selection pressure. Table 3 shows the number of days in selection until the next passage, i.e. the time-period that is needed for the cells to achieve a viability of more than 90% and accordingly achieve that the cells can be used for an antibody titer screening.

TABLE 3

Time course of selection in days

| | Without DNA | V-DHFRref (DHFR) | V-wtFRalpha (FRα) | V-mutFRalpha (FRα*) |
|---|---|---|---|---|
| 50 nM FA | 12 | 12 | 12 | 12 |
| 45 nM FA | 12 | 12 | 12 | 12 |
| 35 nM FA | 12 | 12 | 12 | 12 |
| 25 nM FA | 16 | 55 | 20 | 16 |
| 15 nM FA | 55 | 55 | 20 | 16 |
| 5 nM FA | 55 | 55 | 55 | 16 |

Table 3 shows the number of days in selection until the next passage, i.e. the time frame that was needed by the cells to overcome the selection crisis and achieve a viability of more than 90%. As can be seen, at the beginning all cell pools recover when being cultivated in a selective medium comprising 50, 45 or 35 nM folic acid. However, lower folic acid concentrations put a higher selection pressure on the cells, so that only the use of V-mutFRalpha allowed a good recovery and thus viability after 16 days under these very stringent conditions. Here, the population transfected with V-mutRFalpha recovered and showed a viability of more than 90% in a selection medium only comprising 5 nM to 25 nM folic acid. Cells transfected with V-wtFRalpha needed more time and could not recover at the very low folic acid concentrations.

Example 2

Determination of Antibody Productivity

In order to analyze the success of transfection and selection based on the expression of the gene of interest (here a reference antibody), the cells obtained, i.e. selected according to example 1 were cultured as batch cultures in shake flasks for 13 days in order to determine the productivity of the cells after selection. The cells had a viability of more than 90%. On day 13, the antibody concentration in the culture supernatant was determined using protein A affinity chromatography [mg/L]. The results are shown in Table 4.

TABLE 4

Antibody concentration (mAb) in the culture supernatant of the batch-culture (mg/L)

| Vector | Selection | Antibody titer mAb (mg/L) |
|---|---|---|
| V-DHFRref | 125 nM MTX | 28 |
| | 11 µM FA | 6.6 |
| | 50 nM FA | 6.9 |
| | 45 nM FA | 6.9 |
| | 35 nM FA | 10.1 |
| Without DNA | 50 nM FA | 8.2 |
| | 45 nM FA | 8.3 |
| | 35 nM FA | 6.4 |
| | 25 nM FA | 6.7 |
| V-wtFRalpha | 50 nM FA | 7.1 |
| | 45 nM FA | 8.6 |
| | 35 nM FA | 9 |
| | 25 nM FA | 7 |
| | 15 nM FA | 24 |
| V-mutFRalpha | 50 nM FA | 9.4 |
| | 45 nM FA | 11 |
| | 35 nM FA | 13.9 |
| | 25 nM FA | 17.2 |
| | 15 nM FA | 22.1 |
| | 5 nM FA | 26.6 |

The antibody expressed from the introduced expression vectors could be detected in all cell populations. As low amounts of antibody were also determined in pools that were not transfected with DNA, only values over 9 mg/l were determined to be significant. The reference population in 125 nM MTX (standard DHFR/MTX selection system) produced 28 mg/l. The results of the four cell populations transfected with V-wtFRalpha were at higher folic acid concentrations in the range of the background. However, when lowering the folic acid concentration in the culture medium to 15 nM folic acid, the antibody expression was approximately equally high (24 mg/l) as with the reference control V-DHFRref in 125 nM MTX (28 mg/l). This confirms the previous finding that the wild type folate receptor can serve as selection marker and achieves a comparable efficiency to the established DHFR/MTX system, even though no toxic agents are used for selection. The cell pools that were transfected with V-mutFRalpha showed a linear increase in the antibody titer which was dependent on the folic acid concentration in the culture medium. The lower the concentration of folic acid in the culture medium, the higher was the resulting antibody expression rate. Thus, using the mutated folate receptor according to the disclosure as selection marker has advantages over the use of a wild type folate receptor as selection marker.

As the number of integrated transgenes has an important influence on the expression rate, the copy number of the most important elements, namely the light and heavy chains (LC, HC) of the expressed antibody as well as the copy number of the folate receptor (mutated or wild type) was determined using quantitative PCR on the basis of the genomic DNA of the cell pools.

In relation to the measured antibody titer, the copy number can provide indirectly insight regarding the question whether the place of integration into the genome was responsible for a strong or weak expression. The quantitative PCR analysis as performed herein provides an average value of the transgene copy numbers, because no single cell clones, but a population of different cells which survived selection was analysed.

TABLE 5

Copy number determination using quantitative PCR

| parent. CHO | | number of copies per haploid genome (corrected with folate ratio) | | |
|---|---|---|---|---|
| | | copy number HC | copy number LC | FRα/FRα* |
| parent. CHO | Complete medium | 0.0 | 0.0 | 1.48 |
| V-DHFRref | 125 nM MTX | 2.26 | 2.27 | 1.33 |
| | 35 nM FA | 5.50 | 6.82 | 1.45 |
| withoutDNA | 25 nM FA | 0.00 | 0.00 | 1.66 |
| V-wtFRalpha | 50 nM FA | 0.40 | 0.38 | 1.95 |
| | 45 nM FA | 0.89 | 0.90 | 2.48 |
| | 35 nM FA | 1.00 | 0.99 | 2.83 |
| | 25 nM FA | 0.25 | 0.25 | 1.66 |
| | 15 nM FA | 0.88 | 0.75 | 2.62 |
| V-mutFRalpha | 50 nM FA | 1.65 | 1.98 | 2.32 |
| | 45 nM FA | 2.99 | 2.99 | 3.02 |
| | 35 nM FA | 2.47 | 2.86 | 2.91 |
| | 25 nM FA | 3.20 | 4.02 | 3.11 |
| | 15 nM FA | 5.42 | 6.83 | 4.56 |
| | 5 nM FA | 6.20 | 7.33 | 5.18 |

Table 5 shows the results of the quantitative PCR analysis of V-wtFRalpha and V-mutFRalpha transfectants after selection. From the control pools, a pool was analyzed which had survived the highest selection stringency (V-DHFRref: 125 nM MTX, 35 nM folic acid, without DNA: 25 nM folic acid). Furthermore, untransfected CHO cells cultured without selection pressure were analyzed as negative control. Table 5 shows the copy numbers for the light chain and heavy chain as well as the copy number for the folate receptor that was used as selection marker. The values refer to the theoretical genome size of the CHO cells. Table 5 shows that in untransfected CHO cells, as expected, no antibody sequences could be determined. Furthermore, only the endogenous wild type folic receptor alpha copies were determined. The reference control V-DHFRref selected with 125 nM MTX shows on average a two-fold integration of the antibody transgenes. When looking at the population V-DHFRref selected with 35 nM folic acid, a much higher integration of the light and heavy chains of the antibody can be seen. 5.5 copies of the heavy chain and 6.8 copies of the light chain were detected. The copy number of the FR alpha genes is comparable to the parental CHO cells and is attributable to the endogenous alleles.

The pools that were transfected with V-wtFRalpha showed compared to the controls with V-DHFRref only few copies of HC and LC. No concentration-dependent differences were observed. The number of folate receptor copies increased from 50 nM to 35 nM folic acid to 2.8 copies, but then decreasing at 25 nM. Also the pool that was selected with 15 nM folic acid had incorporated on average 2.6 copies of the antibody chains. In contrast, the cell pools transfected with V-mutFRalpha showed an almost linear increase in the gene copies of the antibody chains which was in parallel to the reduction of folic acid in the selection medium. Thus, the lower the concentration of folic acid in the selection medium, the more copy numbers of the LC and HC genes were detected in the selected cells. The copy numbers of the mutated folate receptor alpha gene showed a comparable trend. The pool that was selected using 5 nM folic acid had approximately three times as many copies of the antibody integrated than the reference control V-DHFRref selected with 125 nM MTX.

Example 3

Single Cell Cloning

In order to develop a cell line which stably produces a gene of interest with high yield, it is necessary to select from the obtained population of different producing cells that survived selection according to example 1 the best cell clones which show both, a high antibody expression rate and good cell growth. For this purpose, cell lines were generated from single cells by limiting dilution. Limiting dilution allows obtaining a monoclonal cell population starting from the polyclonal mass of cells that survived the selection according to example 1. This is achieved by setting up a series of increasing dilutions of the parent (polyclonal) cell culture. A suspension of the parent cells is made. Appropriate dilutions are then made, depending on cell number in the starting population. After the final dilutions are produced, a single cell is placed in the well of a cell culture plate and a clone is made from it. Establishing a population of monoclonal cells guarantees a stable antibody expression over a prolonged period of time. Selected cell populations V-wtFRalpha (15 nM folic acid), V-mutFRalpha (5 nM folic acid), V-DHFRref (125 nM MTX) and V-DHFRref (250 nM MTX—from a different transfection) were respectively cloned. Cloning was performed in a complete medium and furthermore, in a corresponding selection medium as was used beforehand for selection. Thus, in the latter case, the selection pressure was maintained during single cell cloning. After successful growth, the clones were at a confluence of more than 70% transferred into 24 well plates and were tested in a batch cultivation (duration 10 days) for their antibody production. During batch cultivation again either complete medium (no selection pressure) or selection medium (selection pressure maintained) was used. The clones were lined up (medium-dependent) from the highest to the lowest expression level. The results are shown in FIGS. 1 to 4.

Shown are the cloning results achieved either in complete medium (not maintaining the selection pressure after selection) and selection medium (selection pressure was maintained after selection). Here, the typical development of a manual cloning procedure is seen. 1-5 high producing cell clones are found and afterwards, the curve is rapidly descending down to low or even no expressing cell clones. Furthermore, within the low producing cell clones, a broad spectrum of cell productivities was observed, wherein however, the majority was below the threshold of 9 mg/l.

Cloning of cells transfected with V-DHFRref (selected with 125 nM MTX) in complete medium and selection medium resulted in 86 clones (53 in complete medium, 33 in selection medium) from 6×96-well plates. The highest producing clone was cultivated in selection medium and produced in the 24-well batch 28.4 mg/l. In 250 ml shake flask (50 ml total) the original polyclonal pool also achieved a titer of 28 mg/l. Cloning of cells transfected with V-DHFRref (selected with 250 nM MTX) in complete medium and selection medium allowed to isolate 76 clones (41 complete medium and 35 selective medium). The three best clones were isolated from cells cultivated in complete medium after selection, otherwise the cells grown in the selective medium showed a higher overall productivity as the clones in complete medium. The starting polyclonal pool had a titer of 27 mg/l, the highest producing cell clone achieved 42 mg/l in a 24 well. Both reference controls show that not necessarily the highest MTX concentration used during selection results in the highest titer. In order to be able to isolate the best clone, it is necessary to analyze a high number of cell clones.

Cells transfected with the vector V-wtFRalpha which comprises the wild type folate receptor alpha as selectable marker (selected with 15 nM folic acid) were also cloned either in complete medium (not maintaining the selection pressure after selection) or in selection medium (thereby maintaining the selection pressure during cloning). The two highest producing clones were isolated in selective medium. The best clone achieved 53 mg/l in a 24 well format. It was remarkable that only 7 clones survived in this selective medium. In complete medium 49 clones survived. The original pool had in a 250 ml shake flask an antibody concentration of approximately 24 mg/l.

Cells transfected with the vector V-mutFRalpha which comprises the mutated folate receptor alpha as selectable marker (selected with 5 nM folic acid) were also cloned either in complete medium (not maintaining the selection pressure after selection) or in selection medium (thereby maintaining the selection pressure after selection during cloning). The two best clones were isolated from complete medium as well as from selective medium. The highest producing clone had a titer of 42 mg/l in the supernatant. Altogether, hundred clones could be transferred into the 24-well plates, thereunder 52 in complete medium and 48 in selective medium. Here, similar results were achieved in selective and complete medium. Table 6 summarizes the productivity rates of the best producing clones.

TABLE 6

Overview about the highest producing clones (mAb [mg/L]) after endpoint dilution

| | |
|---|---|
| V-wtFRalpha 15 nM FA | 53.5 |
| V-mutFRalpha 5 nM FA | 42.1 |
| V-DHFRref 125 nM MTX | 28.4 |
| V-DHFRref 250 nM MTX | 41.6 |

Table 6 shows that selection with the two selectable markers wild type folate receptor alpha (V-wtFRalpha) and mutated folate receptor alpha (V-mutFRalpha) provided after single cell cloning cell clones that achieved in the performed cloning experiment at least equally good results as the reference selectable marker DHFR. Further experiments (see below) show that also higher overall productivity rates can be obtained when using the mutated folate receptor according to the present disclosure as selectable marker.

Example 4

Co-Transfection Experiments

In order to analyze the selection stringency and efficiency of a double-selection pressure in form of a folic acid deprivation in the selection medium and MTX addition, the cells were co-transfected with V-DHFRref and V-mutFRalpha. All transfected vectors comprised the same antibody genes as protein of interest. Two separate expression vectors were co-transfected, wherein each vector comprised the expression cassettes for expressing the light and the heavy chain of the antibody. Prior to transfection, the CHO cells (except for the cells that were used for the DHFR reference control) were washed three times with PBS in order to reduce folic acid carryover from complete medium and were passaged to selective medium for transfection. The passage of the CHO cells used for transfection of the reference control V-DHFRref was performed in complete medium.

The vectors were transfected into the cells using nucleofection. In contrast to the single vector transfections, the double amount of cells ($1 \times 10^7$ LZ/ml) and the double amount of DNA (per vector 3 µg) was transfected for co-transfection. On a per cell basis, the transfected DNA amount was, however, the same. CHO cells that were transfected with V-DHFRref/V-mutFRalpha and controls were transferred into selective medium; the reference transfections were transferred into complete medium. Selection started 48 hours after transfection. Three transfections per test setting were combined after 48 h, centrifuged and resuspended in 9 ml selection medium or complete medium and were portioned as triplets to the three selection media. Three batches of co-transfected cell pools and controls were exposed to three different concentrations of folic acid/MTX for selection. In parallel thereto, the reference control was performed with the vector V-DHFRref using a G418/MTX selection. Here, the cells were cultivated in complete medium which comprises folic acid in affluence. For starting the selection cycle, the selective agents were then added to induce the selection pressure. As negative control a transfection without the addition of DNA was performed. The performed transfection and used culture media are summarized in subsequent table 7.

TABLE 7

Overview over the performed co-transfections

| Vector | Meaning | Medium before/after transfection | Selection conditions |
|---|---|---|---|
| V-mutFRalpha + V-DHFRref | FRmut + DHFR | Folic acid selective medium | FA/MTX [nM]: 50/50, 50/100 or 12.5/50 |
| no DNA | negative control | Folic acid selective medium | FA/MTX [nM]: 50/50, 50/100 or 12.5/50 |
| V-DHFRref | positive control | complete medium | 0.8 mg/ml G-418, followed by 500 nM and 1 µM MTX |

After selection was completed, batch cultures were prepared from the selected cells in order to determine the expression rate of the integrated antibody genes. During batch cultivation, the cell populations were cultivated in complete medium. In all cell populations antibody concentrations were determined after 13 days of batch cultivation for the co- and reference transfection using protein A affinity chromatography in order to determine the antibody expression. The results are shown in table 8, wherein the batch cultures are named after their origin in the selection medium, i.e. they are named after the performed selection (50/50, 50/100, 12.5/50 [nM FA/nM MTX] or V-DHFRref-G418-MTX—performed in triplets). Cell pools that did not survive are not shown. Again, due to the used measurement method, only values above 9 mg/l are deemed to be significant.

TABLE 8

Antibody concentration (mAb) in the culture supernatant of the Batch-culture in [mg/L]

| Vector transfections and selection conditions | mAb mg/L |
|---|---|
| V-mutFRalpha/V-DHFRref - FA/MTX [nM]: 50/50 (cell pool 1) | 17.7 |
| V-mutFRalpha/V-DHFRref - FA/MTX [nM]: 50/50 (cell pool 2) | 25.6 |
| V-mutFRalpha/V-DHFRref - FA/MTX [nM]: 50/50 (cell pool 3) | 21.5 |
| V-mutFRalpha/V-DHFRref - FA/MTX [nM]: 50/100 (cell pool 1) | 35.8 |

TABLE 8-continued

Antibody concentration (mAb) in the culture supernatant of the Batch-culture in [mg/L]

| Vector transfections and selection conditions | mAb mg/L |
|---|---|
| V-mutFRalpha/V-DHFRref - FA/MTX [nM]: 50/100 (cell pool 2) | 15.4 |
| V-mutFRalpha/V-DHFRref - FA/MTX [nM]: 12.5/50 (cell pool 1) | 34.4 |
| V-mutFRalpha/V-DHFRref - FA/MTX [nM]: 12.5/50 (cell pool 2) | 24.7 |
| V-mutFRalpha/V-DHFRref - FA/MTX [nM]: 12.5/50 (cell pool 3) | 5.9 |
| V-DHFRref - G418-MTX (cell pool 1) | 55 |
| V-DHFRref - G418-MTX (cell pool 2) | 21 |
| V-DHFRref - G418-MTX (cell pool 3) | 57.2 |

As can be seen from table 8, the pools of the DHFR reference method produced after the three selection steps (0.8 mg/ml G418-500 nM MTX-1 µM MTX) up to 58 mg/l antibody titer. From the co-transfection using V-mutFRalpha/V-DHFRref almost all cell pools survived when the cells were transferred after selection in complete medium. The V-mutFRalpha/V-DHFRref pools originating from the 50/50 selection medium produced up to 25 mg/l, the pools—50/100 and the 12.5/50 populations produced titers up to 36 mg/l.

Three consecutive selection cycles were used in the DHFR reference method, because a G418 selection was followed by two MTX selection cycles (500 nM and 1 µM MTX). Therefore, it was additionally tested whether the expression rates can be increased when performing two selection cycles using a limiting concentration of folic acid and MTX in the cell culture medium. Therefore, after performing the first selection cycle using a limiting concentration of folic acid and MTX (regarding the used concentrations see above), cells were transferred into a complete medium to allow recovery. Afterwards, the cells were again exposed in a second selection cycle to the same selective medium and hence to the same selection pressure. The results are shown in Table 9.

TABLE 9

Antibody concentration (mAb) in the culture supernatant of the Batch-culture in [mg/L] after performing two selection cycles

| Vector transfections and selection conditions | mAb mg/L |
|---|---|
| V-mutFRalpha/V-DHFRref - FA/MTX [nM]: 50/50 (cell pool 1) | 388.5 |
| V-mutFRalpha/V-DHFRref - FA/MTX [nM]: 50/50 (cell pool 2) | 72.4 |
| V-mutFRalpha/V-DHFRref - FA/MTX [nM]: 50/50 (cell pool 3) | 667.9 |
| V-mutFRalpha/V-DHFRref - FA/MTX [nM]: 50/100 (cell pool 1) | 132.3 |
| V-mutFRalpha/V-DHFRref - FA/MTX [nM]: 12.5/50 (cell pool 1) | 230.3 |
| V-mutFRalpha/V-DHFRref - FA/MTX [nM]: 12.5/50 (cell pool 2) | 105.4 |
| V-mutFRalpha/V-DHFRref - FA/MTX [nM]: 12.5/50 (cell pool 3) | 8.6 |

Table 9 shows that when the cells transfected with V-mutFRalpha/V-DHFRref were again exposed to selection pressure after 35-38 days, the cells showed a very high significant increase in the production from 21 to 670 mg/l. This is a thirtyfold increase in the antibody titer. Also the other population in 50/50 selection medium produced under repeated selection pressure 20 times more than the culture cultivated in complete medium. Furthermore, the obtained results were significantly better than with the DHFR reference method (see table 8), wherein three selection cycles were performed. Therefore, this selection principle, wherein two selection cycles are performed using a selective medium comprising a limiting concentration of folate and an antifolate with an intermediate cultivation step in non-selective medium resulted in extraordinary high expression titers.

Example 5

Single Cell Cloning

Figure 5:
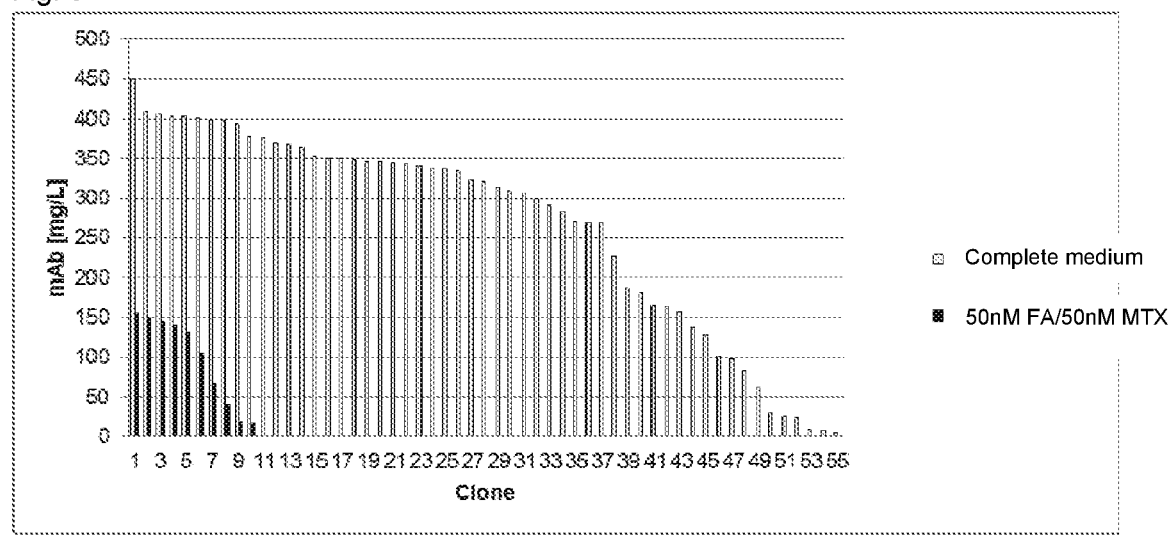

In order to generate cell lines with a stable vector expression, the cell populations obtained according to example 4 were cloned after the selection was completed. After selection, a polyclonal transfection pool 50/50 was cloned using limiting dilution in complete medium (thereby not maintaining the selection pressure during cloning) and selection medium (thereby maintaining the selection pressure during cloning) in 6×96-well plates. After successful growth of the clones, the clones were transferred at a confluence of more than 70% in 24-well plates and were tested after 10 days of batch cultivation for their antibody productivity. The results achieved when cloning the V-mutFRalpha/V-DHFRref co-transfected and selected population are shown in FIG. 5. As shown in FIG. 5, cloning of the V-mutFRalpha/V-DHFRref cells in complete medium and selection medium resulted in 65 clones (55 complete medium, 10 selective medium comprising 50 nM FA/50 nM MTX) from the 6×96-well plates. The clones were lined up (medium-dependent) from the highest to the lowest expression level. The highest producing clone was isolated from cloning in the complete medium and produced in the 24-well batch 450 mg/l. In 250 ml shake flask (50 ml total) the original pool achieved a titer of 670 mg/l.

As reference, a limiting dilution cloning of the DHFR vector V-DHFRref after previous G418-MTX selection was performed. The respective results were obtained from a previous experiment and were performed under similar conditions. Cloning was performed in the selection medium, thereby maintaining the selection pressure during cloning. The results are shown in Table 10.

TABLE 10

Cloning of V-DHFRref-transfected reference-pool

| Clone | mAB (mg/l) |
|---|---|
| 2F1 | 51 |
| 2E8 | 29 |
| 1C11 | 17 |
| 1E10 | 16 |
| 2H8 | 12 |
| 1B10 | 10 |
| 2C3 | 10 |
| 1G7 | 7 |
| 2E3 | 7 |
| 2E10 | 6 |
| 1C9 | 4 |
| 1C10 | 4 |
| 1D1 | 4 |
| 1D5 | 4 |
| 1D10 | 4 |
| 1E3 | 4 |
| 1E7 | 4 |
| 1F1 | 4 |
| 1F7 | 4 |
| 1G6 | 4 |
| 2A2 | 4 |
| 2B6 | 4 |
| 2C5 | 4 |
| 2C8 | 4 |
| 2D6 | 4 |
| 2D9 | 4 |
| 2F6 | 4 |
| 2F8 | 4 |

TABLE 10-continued

Cloning of V-DHFRref-transfected reference-pool

| Clone | mAB (mg/l) |
|---|---|
| 2F9 | 4 |
| 2F10 | 4 |
| 2G2 | 4 |
| 2G7 | 4 |
| 2G9 | 4 |

Here, a gradual G-418 500 nM MTX 1 µM-MTX selection was performed. Table 10 shows the results of an endpoint dilution of the population in selection medium (1 µM MTX). The clones are lined up from the highest to the lowest expression level. The highest producing clone of this reference achieved 51 mg/l in the 20-well batch. A large spectrum of cell productivities were achieved, which, however, lied mostly under the threshold of 9 mg/l.

The results shown in FIG. 5 and Table 10 show that a co-transfection with V-mutFRalpha/V-DHFRref resulted in significantly higher productivities and furthermore, the number of isolated high producing cell clones was significantly increased. More than 50% of the clones isolated from the selected polyclonal population achieved a titer that was higher than 300 mg/l. The co-transfection under the highest selection stringency achieved a nine fold increase in the antibody concentration within the top producing cell clones of V-mutFRalpha, V-DHFRref (different selection methods) and V-mutFRalpha/V-DHFRref. The results are shown in Table 11.

TABLE 11

Overview of the highest producing clones

| | |
|---|---|
| V-mutFRalpha/V-DHFRref (50/50) | 449.3 |
| V-mutFRalpha (5 nM FA) | 42.1 |
| V-DHFRref (125 nM MTX) | 28.4 |
| V-DHFRref (250 nM MTX) | 41.6 |
| V-DHFRref (1 µM MTX) | 51 |

Table 11 shows the antibody concentration (mAb [mg/L]) of the top producers of the performed selections after cloning. As can be seen, co-transfection of V-mutFRalpha/V-DHFRref and selection in a selection medium comprising a limited concentration of folic acid and additionally comprising an antifolate provided the best results.

The above results show that a selection that is based on the use of a mutated folate receptor as selectable marker enabled the survival of successfully transfected cells when using a selection medium comprising a limiting amount of folate, here folic acid. The selection using the mutated folate receptor alpha as selection marker was faster than when using the wild type folate receptor alpha as selection marker. Because the wild type folate receptor alpha binds with a high affinity to folic acid (KD=0.1 nM), the selection pressure is high below the tolerated folic acid threshold concentration under which also cells transfected without DNA could survive. This is also mirrored in the determined antibody concentration. The cells that were transfected with the mutated folate receptor could survive in all tested selective media. Furthermore, a relatively homogenous growth was observed. In the three highest concentrated culture media, the cells could be passaged after 12 days; in the three media with the lowest folic acid concentration recovery was achieved by day 16. In these cases, the selection pressure onto the cells was compared to the wild type folate receptor even further increased. Because the overexpression of the mutated folate receptor is correlated to the expression of the protein of interest, the determined antibody titer is inverse proportional to the folic acid concentration in the selection medium.

Example 6

Transfection of Vectors with dhfr, Wild Type FoIR and FoIR A49L as Selectable Markers In this example, different selection conditions were tested and compared. CHO cells were transfected with the vectors V-DHFRref, V-wtFRalpha and V-mutFRalpha (A49L mutant). A limiting concentration of folic acid in the selection medium was used to create a selection pressure on the host cells, herein also referred to as folic acid deprivation.

Cell cultivation, transfection and screening were carried out in shake flasks using suspension growing CHO cells in a chemically defined culture medium. Cells were transfected by electroporation (nucleofection). For folic acid deprivation based selection, cells were passaged to a folic acid free medium 3 days prior to transfection and were transfected in folic acid free medium to reduce internal folic acid reservoirs. Depending on the cell viability, selection was started 24-48 h after transfection by adding the selective medium to the cells.

V-wtFRalpha and V-mutFRalpha transfected cells were selected using 6 different folic acid concentrations (11700, 150, 50, 5, 0.5 and 0 nM) while in case of V-DHFRref transfected cells 6 different MTX concentrations were tested as reference (2000, 1000, 500, 250, 125 and 0 nM).

After the cells recovered to a viability of above 80% after selection, the productivity of the surviving cell population was analyzed. Productivity of the selected cell populations was analyzed after selection via overgrown shake flask batch cultures in a complete medium containing 11.7 µM folic acid. Batch cultures were seeded in shake flasks (125) with 50 ml working volume and cultivated in a shaker cabinet (not humidified) at 150 rpm and 10% $CO_2$. Viability of cells had to be >90% when starting the assay. The seeding cell density was $2 \times 10^5$ c/ml. Titer determination took place at day 13. Antibody titers in the cell culture supernatant was determined by protein-A HPLC 13 days after starting the culture.

The results of this experiment are described in the following. To evaluate the selection stringency of both folate receptor variants under limiting folic acid concentrations, a variety of folic acid concentrations ranging from 11700 nM (reference medium, complete medium) to 0 nM were tested to select antibody overexpressing cells. In parallel, different MTX concentrations were tested with the reference DHFR vector to compare the performance. All transfected cell populations could be recovered. The ones at 0 nM folic acid presumably contained some traces of folic acid that was carried over from the pre-culture medium. These residual amounts of folic acid were apparently sufficient to promote survival of a sub portion of cells. However, subsequent feeding of folic acid containing medium was necessary to recover those populations. Productivity was assessed as described above. Table 12 summarizes the productivity results.

TABLE 12

Productivity of cell populations after selection

| Folic Acid (nM) | mAb (mg/L) V-wtFRalpha | mAb (mg/L) V-mutFRalpha | MTX (nM) | mAB (mg/L) V-DHFRref |
|---|---|---|---|---|
| 11700.00 | 7 | 10 | 2000.0 | 17 |
| 150.00 | 11 | 12 | 1000.0 | 15 |
| 50.00 | 11 | 19 | 500.0 | 37 |
| 5.00 | 28 | 27 | 250.0 | 37 |
| 0.50 | 17 | 32 | 125.0 | 18 |
| 0.00 | 11 | 136 | 0.0 | 8 |

Table 12 shows the results for transfected cells selected at different folic acid or MTX concentrations that were analyzed in shake flask batch cultures. At day 13 of the culture, samples of the culture medium were taken and analyzed for antibody content by Protein-A HPLC. It was found that all cell populations produce antibody. With V-wtFRalpha, a maximum of productivity was achieved when selecting at 5 nM folic acid. This concentration of folic acid is lower than the concentration observed in the above experiments and is probably attributable to the fact that some folic acid was carried over from the initial culture medium in this example. This would also explain the recovery and production rates achieved at OnM folic acid. Further reduction of folic acid did not lead to higher productivity when using the wild type folate receptor. In contrast, with V-mutFRalpha, a higher productivity is achieved with the lowest folic acid concentration during selection. The productivity achieved with the mutant is significantly higher than the productivity achieved with the wild type folate receptor and is also significantly higher as with DHFR/MTX.

Furthermore, when analysing the recovery of the cells during selection it was found that cells transfected with V-mutFRalpha recovered significantly faster under very low folic acid concentrations, in particular <25 nM. Therefore, the faster recovery rates described above were also confirmed in this experiment.

The above described examples 1 to 6 demonstrate the advantages that are achieved with the teachings of the present disclosure, wherein a mutated folate receptor is used for selection. E.g., in the above described examples the reference population (DHFR) an antibody secretion of 28 mg/l was determined, with the highest survival selection stringency of V-wtFRalpha transfected cells 24 mg/l was obtained and with the V-mutFRalpha transfected cells 26.6 mg/l was obtained. Therefore, the productivity rates determined in the respective experiment were in a similar range, which shows that the wild typewild type folate receptor alpha as well as the mutated folate receptor alpha achieves as selectable markers comparable results to the established DHFR/MTX selection system which can be perceived as "gold standard". Furthermore, when comparing the time periods necessary for selection it was observed that a significantly faster selection is possible with a mutated folate receptor based selection system as provided by the present disclosure. Even the cells transfected with the V-wtFRalpha vector in 15 nM folic acid and 25 nM folic acid which needed a longer recovery phase than V-mutFRalpha transfected cells at the same concentration (16 days) showed with 20 days a clear advantage over the reference control (DHFR), which are at this point in time still in crisis. Using the folate receptor mutant according to the present disclosure thus allows compared to the DHFR/MTX system to save time during the selection phase in the cell line development and is also faster than the wild type based selection system. The results also indicate that using the mutated folate receptor provides the cells with an advantage compared to using the wild type folate receptor in the tested selective media, because the cells survive a larger folic acid concentration window and in particular can survive lower folic acid concentrations, thereby allowing more stringent selection conditions. Furthermore, the selection crisis is recovered significantly earlier with the mutated folate receptor than is the case with the cells that were transfected with the wild type folate receptor. The results show that using a mutated folate receptor as described herein has important advantages.

Furthermore, also the experiments wherein a double selection against the folate receptor and DHFR as selectable markers was performed using a selection medium comprising folate in a limiting concentration and additionally comprising an antifolate, showed clear advantages for the mutated folate receptor. The mutation in the folate receptor apparently has a positive effect on the cell growth under said double selection pressure. Without being bound by theory, it could be that the affinity to anti-folates such as MTX is reduced in the mutant, so that less MTX is incorporated into the cells. Furthermore, it was found that it is advantageous to repeat the selection and transfer the cells into a complete medium in-between two selection cycles in order to allow the cells to recover after the first selection round. After retransferring the cells into the selection medium, it was possible to enrich the cells which have integrated both vectors into their genome and therefore were able to survive the double selection pressure. It was found that the productivity was increased compared to the complete medium up to twenty to thirtyfold. This is a significant advantage. Compared to the reference control after a standard G418/MTX multi-step selection, still a six- to thirteen fold increase in the productivity was observed. Therefore, the selection system according to the present disclosure wherein a mutated folate receptor is used in combination with DHFR has clear advantages over prior art selection system. Furthermore, using this double selection strategy more than 50% high producing clones having a titer above 300 mg/l could be singled out. Therefore, the search for very high producing clones was less cumbersome, what is a significant improvement over existing screening technologies in particular for the purpose of industrial protein production.

The mutated folate receptor that is according to the present disclosure used as selection marker is highly advantageous, because the transfected populations survive the growth crisis quicker than the reference selection systems. Furthermore, cell populations that were transfected with the mutant folate receptor showed after selection in different selective media a receptor and antibody expression that was inverse proportional to the concentration of folic acid. This correlation could be shown using molecular biological analysis of the genomic DNA (copy number) as well as on the RNA level. Furthermore, it was found that using a mutated folate receptor as described herein is highly advantageous when pursuing a co-selection with DHFR/MTX. The used controls (single transfections of FRwt, FRmut and DHFR) could not survive the lethal effect of a stringent combination of folic acid deprivation and MTX. The high stringency of this selection system also had the effect though, that some of the co-transfected populations were selected out. However, by adding folic acid as intermediate step and performing a second selection round, very good results were achieved with the co-transfection principle when using a double selection principle with FRmut/DHFR. It was shown that this method allows a quicker and less cumbersome screening for best producing (top) clones. Single cell cloning of the highest producing cell population (670 mg/l in 50 ml culture volume) resulted in an approximate 50% recovery of high producing cell clones that produced more than 300 mg/l. Compared to the single transfection and the reference, the cloning of the co-transfected population achieved an average productivity of 240 mg/l, which is a fortyfold increase in the productivity. The top producing cell clone achieved 450 mg/l in a 24-well batch. These results confirm that the present disclosure which is based on the use of a mutated folate receptor as selection marker makes a significant contribution to existing selection systems.

Example 7

Transfection of an Expression Vector Comprising Two Selectable Markers

In this example, CHO cells were transfected (nucleofection) with an expression vector which comprised an expression cassette comprising a polynucleotide encoding a mutated human folate receptor alpha (A49L mutant—mutFRalpha, see above) and an expression cassette comprising a polynucleotide encoding DHFR (V-mutFRalpha/DHFRref). Thus, both selectable markers mutFRalpha and DHFR were on the same expression vector.

Furthermore, the expression vector comprised an expression cassette comprising a polynucleotide encoding the light chain of an antibody and an expression cassette comprising a polynucleotide encoding the heavy chain of an antibody. In this experiment, a different antibody was expressed than in the previous examples. Five different selection conditions using 50 nM folic acid (FA) and different concentrations of MTX were tested. The selection media are summarized in subsequent Table 13. After selection, the selected cell pools were transferred to complete medium and grown in shake flask batch cultures. At day 13 of the culture, samples of the culture medium were taken and analyzed for antibody content by Protein-A HPLC. The results are also shown in Table 13.

As can be seen, a MTX concentration already as low as 5 nM provided a significant selection advantage when using the expression vector V-mutFRalpha/DHFRref which comprises a mutated folate receptor and DHFR as selectable marker. This confirms the advantages of using the mutated folate receptor in combination with DHFR for selection that were also shown in the other examples. The antibody productivities are significantly increased and furthermore, lower concentrations of MTX can be used during selection which is a significant advantage considering that MTX is a toxic agent.

Example 8

Transfection with Simplified Pre-Treatment of Parental CHO Cells

In order to test if it is possible to avoid cell centrifugation/washing steps in the procedure, parental CHO cells were taken in culture using culture media containing a limiting concentration of 50 nM folic acid, either from cells cryopreserved in full medium or medium with 50 nM folic acid. After several passages in this medium, cells were transfected using the nucleofection method and expression vector V-mutFRalpha/DHFRref encoding a monoclonal antibody. This transfection and subsequent culture was done using the same medium with 50 nM folic acid. Then, 48 h after transfection, selection pressure was increased by adding 10 nM MTX to the culture. Productivitiy of cultures recovered from selection was assessed in shake flaks batch cultures using complete medium. The results are shown in Table 14. As shown in Table 14, such simplified protocols for transfection and selection procedures result in comparable productivities to procedures in previous examples (e.g. Table 13).

TABLE 13

Pool productivity obtained with expression vector V-mutFRalpha/DHFRref using different selection conditions

| Selection condition | Antibody concentration [mg/L] |
| --- | --- |
| 50 nM FA/50 nM MTX | 1360 |
| 50 nM FA/10 nM MTX | 1250 |
| 50 nM FA/5 nM MTX | 180 |
| 50 nM FA/1 nM MTX | 80 |
| 50 nM FA/no MTX | 80 |

TABLE 14

Pool productivity obtained with expression vector V-mutFRalpha/DHFRref using different selection conditions.

| Parental cell source | mAb concentration (mg/L) (average of 2 replicates) |
| --- | --- |
| Parental cells frozen in full media | 1326 |
| Parental cells frozen in media containing 50 nM folic acid | 1232 |

The invention claimed is:

1. A process for producing a polypeptide, comprising:
   a) culturing a host cell under conditions that allow for the expression and secretion of the polypeptide, wherein the viability of said host cell is dependent on folate uptake, wherein the host cell comprises:
      i) an introduced polynucleotide encoding a selectable marker, wherein the selectable marker is a mutated folate receptor alpha, and
      ii) at least one introduced polynucleotide encoding the polypeptide, wherein said polypeptide is secreted from said host cell;
   b) isolating the polypeptide from the cell culture medium; and
   c) optionally processing the isolated polypeptide,
   wherein the mutated folate receptor alpha consists of the amino acid sequence shown in SEQ ID NO:1, wherein alanine is substituted to leucine at amino acid position 49, and
   wherein the host cell cultured in step a) is a host cell selected according to a method for selecting at least one host cell expressing a polypeptide, wherein said method comprises:
   a. providing a plurality of host cells, wherein the viability of said plurality of host cells is dependent on folate uptake, and wherein said plurality of host cells comprises:
      i) the introduced polynucleotide encoding the selectable marker, and
      ii) the at least one introduced polynucleotide encoding a polypeptide;
   b. culturing said plurality of host cells in a selective culture medium comprising folate at a concentration of 50 nM or less, which provides a stringent selective pressure on the host cell; and
   c. obtaining at least one host cell expressing the polypeptide.

2. The process of claim 1, wherein the host cell comprises an expression vector or combination of at least two expression vectors comprising:
   a) an expression cassette comprising the polynucleotide encoding the mutated folate receptor alpha;
   b) at least one expression cassette comprising the polynucleotide encoding the polypeptide; and
   c) an expression cassette comprising a polynucleotide encoding a dihydrofolate reductase as selectable marker.

3. The process of claim 1, wherein the host cell has one or more of the following characteristics:
   a) it is a mammalian cell;
   b) it is a rodent cell;
   c) it is a CHO cell;
   d) it expresses an endogenous folate receptor;
   e) it comprises an introduced polynucleotide encoding a further selectable marker, wherein the further selectable marker is involved in folate metabolism, and wherein the further selectable marker optionally is a dihydrofolate reductase; and/or
   f) the introduced polynucleotides are stably integrated into the genome.

4. The process of claim 1, wherein the host cell comprises an expression vector or combination of at least two expression vectors comprising:
   i) the introduced polynucleotide encoding the mutated folate receptor alpha as the selectable marker, and
   ii) the at least one introduced polynucleotide encoding the polypeptide.

5. The process of claim 1, wherein the method for selecting at least one host cell expressing a polypeptide has one or more of the following characteristics:
   i) additional selection cycles comprising steps b. and c. are performed;
   ii) after step c., the cells are cultured in a culture medium comprising a non-limiting concentration of folate and are then again cultured according to step b. and obtained according to step c;
   iii) one or more additional selection steps are performed prior to and/or after performing step b. and/or c., wherein said one or more additional selection steps are selected from a flow cytometry based selection and a selection for one or more additional selectable markers introduced into the host cell;
   iv) the host cells are stably transfected; and
   v) the selected host cells recombinantly express and secrete the polypeptide, wherein the polypeptide is an immunoglobulin molecule.

6. The process of claim 1, wherein the selectable marker allows a more stringent and faster selection of high producers than a selection system which uses the corresponding wild type folate receptor alpha as selectable marker.

* * * * *

SEQUENCE LISTING

<160> NUMBER OF SEQ ID NOS: 13

<210> SEQ ID NO 1
<211> LENGTH: 205
<212> TYPE: PRT
<213> ORGANISM: Homo sapiens

<400> SEQUENCE: 1

Ile Ala Trp Ala Arg Thr Glu Leu Leu Asn Val Cys Met Asn Ala Lys
1               5                   10                  15

His His Lys Glu Lys Pro Gly Pro Glu Asp Lys Leu His Glu Gln Cys
            20                  25                  30

Arg Pro Trp Arg Lys Asn Ala Cys Cys Ser Thr Asn Thr Ser Gln Glu
            35                  40                  45

Ala His Lys Asp Val Ser Tyr Leu Tyr Arg Phe Asn Trp Asn His Cys
 50                  55                  60

Gly Glu Met Ala Pro Ala Cys Lys Arg His Phe Ile Gln Asp Thr Cys
 65                  70                  75                  80

Leu Tyr Glu Cys Ser Pro Asn Leu Gly Pro Trp Ile Gln Gln Val Asp
                 85                  90                  95

Gln Ser Trp Arg Lys Glu Arg Val Leu Asn Val Pro Leu Cys Lys Glu
            100                 105                 110

Asp Cys Glu Gln Trp Trp Glu Asp Cys Arg Thr Ser Tyr Thr Cys Lys
            115                 120                 125

Ser Asn Trp His Lys Gly Trp Asn Trp Thr Ser Gly Phe Asn Lys Cys
130                 135                 140

Ala Val Gly Ala Ala Cys Gln Pro Phe His Phe Tyr Phe Pro Thr Pro
145                 150                 155                 160

Thr Val Leu Cys Asn Glu Ile Trp Thr His Ser Tyr Lys Val Ser Asn
                165                 170                 175

Tyr Ser Arg Gly Ser Gly Arg Cys Ile Gln Met Trp Phe Asp Pro Ala
            180                 185                 190

Gln Gly Asn Pro Asn Glu Glu Val Ala Arg Phe Tyr Ala
            195                 200                 205

<210> SEQ ID NO 2
<211> LENGTH: 27
<212> TYPE: PRT
<213> ORGANISM: Homo sapiens

<400> SEQUENCE: 2

Ala Ala Met Ser Gly Ala Gly Pro Trp Ala Ala Trp Pro Phe Leu Leu
 1               5                  10                  15

Ser Leu Ala Leu Met Leu Leu Trp Leu Leu Ser
            20                  25

<210> SEQ ID NO 3
<211> LENGTH: 257
<212> TYPE: PRT
<213> ORGANISM: Homo sapiens

<400> SEQUENCE: 3

Met Ala Gln Arg Met Thr Thr Gln Leu Leu Leu Leu Leu Val Trp Val
 1               5                  10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
            115                 120                 125

```
Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 4
<211> LENGTH: 203
<212> TYPE: PRT
<213> ORGANISM: Homo sapiens

<400> SEQUENCE: 4

Gln Asp Arg Thr Asp Leu Leu Asn Val Cys Met Asp Ala Lys His His
1               5                   10                  15

Lys Thr Lys Pro Gly Pro Glu Asp Lys Leu His Asp Gln Cys Ser Pro
            20                  25                  30

Trp Lys Lys Asn Ala Cys Cys Thr Ala Ser Thr Ser Gln Glu Leu His
        35                  40                  45

Lys Asp Thr Ser Arg Leu Tyr Asn Phe Asn Trp Asp His Cys Gly Lys
    50                  55                  60

Met Glu Pro Ala Cys Lys Arg His Phe Ile Gln Asp Thr Cys Leu Tyr
65                  70                  75                  80

Glu Cys Ser Pro Asn Leu Gly Pro Trp Ile Gln Gln Val Asn Gln Thr
                85                  90                  95

Trp Arg Lys Glu Arg Phe Leu Asp Val Pro Leu Cys Lys Glu Asp Cys
            100                 105                 110

Gln Arg Trp Trp Glu Asp Cys His Thr Ser His Thr Cys Lys Ser Asn
        115                 120                 125

Trp His Arg Gly Trp Asp Trp Thr Ser Gly Val Asn Lys Cys Pro Ala
    130                 135                 140

Gly Ala Leu Cys Arg Thr Phe Glu Ser Tyr Phe Pro Thr Pro Ala Ala
145                 150                 155                 160

Leu Cys Glu Gly Leu Trp Ser His Ser Tyr Lys Val Ser Asn Tyr Ser
                165                 170                 175

Arg Gly Ser Gly Arg Cys Ile Gln Met Trp Phe Asp Ser Ala Gln Gly
            180                 185                 190

Asn Pro Asn Glu Glu Val Ala Arg Phe Tyr Ala
        195                 200

<210> SEQ ID NO 5
<211> LENGTH: 31
<212> TYPE: PRT
<213> ORGANISM: Homo sapiens
```

<400> SEQUENCE: 5

Ala Ala Met His Val Asn Ala Gly Glu Met Leu His Gly Thr Gly Gly
1               5                   10                  15

Leu Leu Leu Ser Leu Ala Leu Met Leu Gln Leu Trp Leu Leu Gly
            20                  25                  30

<210> SEQ ID NO 6
<211> LENGTH: 255
<212> TYPE: PRT
<213> ORGANISM: Homo sapiens

<400> SEQUENCE: 6

Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His
        35                  40                  45

Asp Gln Cys Ser Pro Trp Lys Lys Asn Ala Cys Cys Thr Ala Ser Thr
    50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 7
<211> LENGTH: 223
<212> TYPE: PRT
<213> ORGANISM: Homo sapiens

<400> SEQUENCE: 7

Gln Pro Arg Ser Ala Arg Ala Arg Thr Asp Leu Leu Asn Val Cys Met
1               5                   10                  15

Asn Ala Lys His His Lys Thr Gln Pro Ser Pro Glu Asp Glu Leu Tyr
            20                  25                  30

```
Gly Gln Cys Ser Pro Trp Lys Lys Asn Ala Cys Cys Thr Ala Ser Thr
            35                  40                  45

Ser Gln Glu Leu His Lys Asp Thr Ser Arg Leu Tyr Asn Phe Asn Trp
 50                  55                  60

Asp His Cys Gly Lys Met Glu Pro Thr Cys Lys Arg His Phe Ile Gln
 65                  70                  75                  80

Asp Ser Cys Leu Tyr Glu Cys Ser Pro Asn Leu Gly Pro Trp Ile Arg
                 85                  90                  95

Gln Val Asn Gln Ser Trp Arg Lys Glu Arg Ile Leu Asn Val Pro Leu
            100                 105                 110

Cys Lys Glu Asp Cys Glu Arg Trp Trp Glu Asp Cys Arg Thr Ser Tyr
        115                 120                 125

Thr Cys Lys Ser Asn Trp His Lys Gly Trp Asn Trp Thr Ser Gly Ile
130                 135                 140

Asn Glu Cys Pro Ala Gly Ala Leu Cys Ser Thr Phe Glu Ser Tyr Phe
145                 150                 155                 160

Pro Thr Pro Ala Ala Leu Cys Glu Gly Leu Trp Ser His Ser Phe Lys
                165                 170                 175

Val Ser Asn Tyr Ser Arg Gly Ser Gly Arg Cys Ile Gln Met Trp Phe
            180                 185                 190

Asp Ser Ala Gln Gly Asn Pro Asn Glu Glu Val Ala Lys Phe Tyr Ala
        195                 200                 205

Ala Ala Met Asn Ala Gly Ala Pro Ser Arg Gly Ile Ile Asp Ser
210                 215                 220

<210> SEQ ID NO 8
<211> LENGTH: 245
<212> TYPE: PRT
<213> ORGANISM: Homo sapiens

<400> SEQUENCE: 8

Met Asp Met Ala Trp Gln Met Met Gln Leu Leu Leu Leu Ala Leu Val
 1               5                  10                  15

Thr Ala Ala Gly Ser Ala Gln Pro Arg Ser Ala Arg Ala Arg Thr Asp
             20                  25                  30

Leu Leu Asn Val Cys Met Asn Ala Lys His His Lys Thr Gln Pro Ser
         35                  40                  45

Pro Glu Asp Glu Leu Tyr Gly Gln Cys Ser Pro Trp Lys Lys Asn Ala
     50                  55                  60

Cys Cys Thr Ala Ser Thr Ser Gln Glu Leu His Lys Asp Thr Ser Arg
 65                  70                  75                  80

Leu Tyr Asn Phe Asn Trp Asp His Cys Gly Lys Met Glu Pro Thr Cys
                 85                  90                  95

Lys Arg His Phe Ile Gln Asp Ser Cys Leu Tyr Glu Cys Ser Pro Asn
            100                 105                 110

Leu Gly Pro Trp Ile Arg Gln Val Asn Gln Ser Trp Arg Lys Glu Arg
        115                 120                 125

Ile Leu Asn Val Pro Leu Cys Lys Glu Asp Cys Glu Arg Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Ile Asn Glu Cys Pro Ala Gly Ala Leu Cys Ser
                165                 170                 175

Thr Phe Glu Ser Tyr Phe Pro Thr Pro Ala Ala Leu Cys Glu Gly Leu
            180                 185                 190
```

```
Trp Ser His Ser Phe Lys Val Ser Asn Tyr Ser Arg Gly Ser Gly Arg
            195                 200                 205
Cys Ile Gln Met Trp Phe Asp Ser Ala Gln Gly Asn Pro Asn Glu Glu
210                 215                 220
Val Ala Lys Phe Tyr Ala Ala Ala Met Asn Ala Gly Ala Pro Ser Arg
225                 230                 235                 240
Gly Ile Ile Asp Ser
            245

<210> SEQ ID NO 9
<211> LENGTH: 205
<212> TYPE: PRT
<213> ORGANISM: Artificial
<220> FEATURE:
<223> OTHER INFORMATION: Mature mutated folate receptor
<220> FEATURE:
<221> NAME/KEY: MISC_FEATURE
<222> LOCATION: (49)..(49)
<223> OTHER INFORMATION: Xaa is any amino acid except Ala

<400> SEQUENCE: 9

Ile Ala Trp Ala Arg Thr Glu Leu Leu Asn Val Cys Met Asn Ala Lys
1               5                   10                  15
His His Lys Glu Lys Pro Gly Pro Glu Asp Lys Leu His Glu Gln Cys
            20                  25                  30
Arg Pro Trp Arg Lys Asn Ala Cys Cys Ser Thr Asn Thr Ser Gln Glu
        35                  40                  45
Xaa His Lys Asp Val Ser Tyr Leu Tyr Arg Phe Asn Trp Asn His Cys
    50                  55                  60
Gly Glu Met Ala Pro Ala Cys Lys Arg His Phe Ile Gln Asp Thr Cys
65                  70                  75                  80
Leu Tyr Glu Cys Ser Pro Asn Leu Gly Pro Trp Ile Gln Gln Val Asp
                85                  90                  95
Gln Ser Trp Arg Lys Glu Arg Val Leu Asn Val Pro Leu Cys Lys Glu
            100                 105                 110
Asp Cys Glu Gln Trp Trp Glu Asp Cys Arg Thr Ser Tyr Thr Cys Lys
        115                 120                 125
Ser Asn Trp His Lys Gly Trp Asn Trp Thr Ser Gly Phe Asn Lys Cys
    130                 135                 140
Ala Val Gly Ala Ala Cys Gln Pro Phe His Phe Tyr Phe Pro Thr Pro
145                 150                 155                 160
Thr Val Leu Cys Asn Glu Ile Trp Thr His Ser Tyr Lys Val Ser Asn
                165                 170                 175
Tyr Ser Arg Gly Ser Gly Arg Cys Ile Gln Met Trp Phe Asp Pro Ala
            180                 185                 190
Gln Gly Asn Pro Asn Glu Glu Val Ala Arg Phe Tyr Ala
        195                 200                 205

<210> SEQ ID NO 10
<211> LENGTH: 25
<212> TYPE: PRT
<213> ORGANISM: Homo sapiens

<400> SEQUENCE: 10

Met Ala Gln Arg Met Thr Thr Gln Leu Leu Leu Leu Leu Val Trp Val
1               5                   10                  15
Ala Val Val Gly Glu Ala Gln Thr Arg
            20                  25
```

```
<210> SEQ ID NO 11
<211> LENGTH: 21
<212> TYPE: PRT
<213> ORGANISM: Homo sapiens

<400> SEQUENCE: 11

Met Val Trp Lys Trp Met Pro Leu Leu Leu Leu Val Cys Val Ala
1               5                   10                  15

Thr Met Cys Ser Ala
            20

<210> SEQ ID NO 12
<211> LENGTH: 22
<212> TYPE: PRT
<213> ORGANISM: Homo sapiens

<400> SEQUENCE: 12

Met Asp Met Ala Trp Gln Met Met Gln Leu Leu Leu Ala Leu Val
1               5                   10                  15

Thr Ala Ala Gly Ser Ala
            20

<210> SEQ ID NO 13
<211> LENGTH: 232
<212> TYPE: PRT
<213> ORGANISM: Artificial
<220> FEATURE:
<223> OTHER INFORMATION: Mutated folate receptor

<400> SEQUENCE: 13

Ile Ala Trp Ala Arg Thr Glu Leu Leu Asn Val Cys Met Asn Ala Lys
1               5                   10                  15

His His Lys Glu Lys Pro Gly Pro Glu Asp Lys Leu His Glu Gln Cys
            20                  25                  30

Arg Pro Trp Arg Lys Asn Ala Cys Cys Ser Thr Asn Thr Ser Gln Glu
        35                  40                  45

Leu His Lys Asp Val Ser Tyr Leu Tyr Arg Phe Asn Trp Asn His Cys
    50                  55                  60

Gly Glu Met Ala Pro Ala Cys Lys Arg His Phe Ile Gln Asp Thr Cys
65                  70                  75                  80

Leu Tyr Glu Cys Ser Pro Asn Leu Gly Pro Trp Ile Gln Gln Val Asp
                85                  90                  95

Gln Ser Trp Arg Lys Glu Arg Val Leu Asn Val Pro Leu Cys Lys Glu
            100                 105                 110

Asp Cys Glu Gln Trp Trp Glu Asp Cys Arg Thr Ser Tyr Thr Cys Lys
        115                 120                 125

Ser Asn Trp His Lys Gly Trp Asn Trp Thr Ser Gly Phe Asn Lys Cys
    130                 135                 140

Ala Val Gly Ala Ala Cys Gln Pro Phe His Phe Tyr Phe Pro Thr Pro
145                 150                 155                 160

Thr Val Leu Cys Asn Glu Ile Trp Thr His Ser Tyr Lys Val Ser Asn
                165                 170                 175

Tyr Ser Arg Gly Ser Gly Arg Cys Ile Gln Met Trp Phe Asp Pro Ala
            180                 185                 190

Gln Gly Asn Pro Asn Glu Glu Val Ala Arg Phe Tyr Ala Ala Ala Met
        195                 200                 205
```

```
Ser Gly Ala Gly Pro Trp Ala Ala Trp Pro Phe Leu Leu Ser Leu Ala
    210                 215                 220

Leu Met Leu Leu Trp Leu Leu Ser
225                 230
```